(12) United States Patent
Lu et al.

(10) Patent No.: US 7,745,571 B2
(45) Date of Patent: Jun. 29, 2010

(54) PEPTIDE INHIBITORS OF IASPP

(75) Inventors: Xin Lu, London (GB); Patricia Kuwabara, Bristol (GB); David Selwood, London (GB)

(73) Assignees: Ludwig Institute for Cancer Research, New York, NY (US); Genome Research Limited, Cambridge (GB); UCL Cruciform Limited, Long (GB)

( * ) Notice: Subject to any disclaimer, the term of this patent is extended or adjusted under 35 U.S.C. 154(b) by 0 days.

(21) Appl. No.: 12/043,058

(22) Filed: Mar. 5, 2008

(65) Prior Publication Data
US 2008/0260756 A1 Oct. 23, 2008

Related U.S. Application Data

(62) Division of application No. 10/522,043, filed as application No. PCT/GB03/04296 on Oct. 3, 2003, now abandoned.

(30) Foreign Application Priority Data

Oct. 7, 2002 (GB) ................................. 0223193.4
Mar. 19, 2003 (GB) ................................. 0306261.9

(51) Int. Cl.
*A61K 38/00* (2006.01)
(52) U.S. Cl. .................................................... 530/300
(58) Field of Classification Search .................. 530/300
See application file for complete search history.

(56) References Cited

U.S. PATENT DOCUMENTS 6,582,933 B1 * 6/2003 Okamoto ................... 435/69.1

FOREIGN PATENT DOCUMENTS

WO   WO 00/55175 A1   9/2000
WO   WO 01/07082 A1 * 2/2001

OTHER PUBLICATIONS

Dippold et al (PNAS, Mar. 1981, 78(3): 1695-1699).*
Amalfitano et al., "Separating fact from fiction: assessing the potential of modified adenovirus vectors for use in human gene therapy," *Current Gene Therapy*, 2:111-133 (2002).
Bergamaschi et al., "iASPP Oncoprotein is a Key Inhibitor of p53 Conserved From Worm to Human," *Nature Genet*. 33:162-167 (2003).
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol*. 111:2129-2138 (1990).
Database NCBI 'Online!' Accession No. NP_006654 (2003).
Database NCBI 'Online!' Accession No. NP_505955 (2003).
Houdebine, "Production of pharmaceutical proteins from transgenic animals," *Jour. of Biotechnology*, 34:269-287 (1994).
Iwabuchi et al., "Stimulation of p53-Mediated Transcriptional Activation by the p53-Binding Proteins, 53BP1 and 53BP2," *J. Biol. Chem*. 273:26061-26068 (1998).
Lazar et al., "Transforming Growth Factor α: Mutation of Aspartic Acid 47 and Leucine 48 Results in Different Biological Activities," *Mol. Cell Biol.*, 8:1247-1252 (1998).
Naumovski and Cleary, "The p53-Binding Protein 53BP2 Also Interacts with Bcl2 and Impedes Cell Cycle Progression at G2/M," *Mol. Cell. Biol*. 16:3884:3892 (1996).
Pandha et al., "Oncological applications of gene therapy," *Current Opinion in Investigational Drugs*, 1(1):122-134 (2000).
Samuels-Lev et al., "ASPP Proteins Specifically Stimulate the Apoptotic Function of p53," *Mol. Cell*, 8:781-794 (2001).
Slee and Lu, "The ASPP Family: Deciding Between Life and Death After DNA Damage," *Toxicol. Lett*. 139:81-87 (2003).
Stiewe et al., "Transactivation-deficient Delta TA-p73 inhibits p53 by direct competition for DNA binding: implications for tumorigenesis," *J. Biol. Chem.*, 277(16):14177-85 (2002).
Takada et al., "ReIA-Associated Inhibitor Blocks Transcription of Human Immunodeficiency Virus Type 1 by Inhibiting NF-κB and Sp1 Actions," *J. Virol*. 76:8019-8030 (2002).
Verma et al., "Gene therapy—promises, problems and prospects," *Nature*, 389:239-242 (1997).

* cited by examiner

*Primary Examiner*—Sean E Aeder
(74) *Attorney, Agent, or Firm*—Marshall, Gerstein & Borun LLP

(57) ABSTRACT

The invention relates to a polypeptide or part thereof which inhibits the apoptotic activity of the tumor suppressor protein p53, and includes screening methods to identify agents which interfere with the activity of the polypeptide.

16 Claims, 18 Drawing Sheets

Figure 1a

```
   1 GCGGCCGCGT CGACCCGGCG TTCAGACGCG GGCAGCTACC GGCGCTCGCT GGGCTCCGCG
  61 GGGCCGTCGG GCACTTTGCC TCGCAGCTGG CAGCCCGTCA GCCGCATCCC CATGCCCCCC
 121 TCCAGCCCCC AGCCCGCGG GGCCCCGCGC CAGCGTCCCA TCCCCCTCAG CATGATCTTC
 181 AAGCTGCAGA ACGCCTTCTG GGAGCACGGG GCCAGCCGCG CCATGCTCCC TGGGTCCCCC
 241 CTCTTCACCC GAGCACCCCC GCCTAAGCTG CAGCCCCAAC CACAACCACA GCCCCAGCCA
 301 CAATCACAAC CACAGCCCCA GCTGCCCCAA CAGCCCCAGA CCCAACCCCA AACCCCTACC
 361 CCAGCCTCCC ACATCCGCAT CCCCAACAGA CATGGCCCCC TGTGAACGAA GGACCCCCCA
 421 AACCCCCCAC CGAGCTGGAG CCTGAGCCGG AGATAGAGGG GCTGCTGACA CCAGTGCTGG
 481 AGGCTGGCGA TGTGGATGAA GGACCCTGTA GCAAGGCCTC TCAGCCCCAC GAGGCTGCAG
 541 CCAGCACTGC CACCGGAGGC ACAGTCGGTG CCCGAGCTGG AGGAGGTGGC ACGGGTGTTG
 601 GCGGAAATTC CCCGGCCCCT CAAACGCAGG GGCTCCATGG AGCAGGCCCC TGCTGTGGCC
 661 CTGCCCCCTA CCCACAAGAA ACAGTACCAG CAGATCATCA GCCGCCTCTT CCATCGTCAT
 721 GGGGGGCCAG GGCCCGGGGG GCGGAGCCAG AGCTGTCCCC CATCACTGAG GGATCTGAGG
 781 CCAGGGCAGG GCCCCCTGCT CCTGCCCCAC CAGCTCCCAT TCCACCGCCC GGCCCCGTCC
 841 CAGAGCAGCC CACCAGAGCA GCCGCAGAGC ATGGAGATGC GCTCTGTGCT GCGGAAGGCG
 901 GGCTCCCCGC GCAAGGCCCG CCGCGCGCGC CTCAACCCTC TGGTGCTCCT CCTGGACGCG
 961 GCGCTGACCG GGGAGCTGGA GGTGGTGCAG CAGGCGGTGA AGGAGATGAA CGACCCGAGC
1021 CAGCCCAACG AGGAGGGCAT CACTGCCTTG CACAACGCCA TCTGCGGCGC CAACTACTCT
1081 ATCGTGGATT TCCTCATCAC CGCGGGTGCC AATGTCAACT CCCCCGACAG CCACGGCTGG
1141 ACACCCTTGC ACTGCGCGGC GTCGTGCAAC GACACAGTCA TCTGCATGGC GCTGGTGCAG
1201 CACGGCGCTG CAATCTTCGC CACCACGCTC AGCGACGGCG CCACCGCCTT CGAGAAGTGC
1261 GACCCTTACC GCGAGGGTTA TGCTGACTGC GCCACCTACC TGGCAGACGT CGAGCAGAGT
1321 ATGGGGCTGA TGAACAGCGG GGCAGTGTAC GCTCTCTGGG ACTACAGCGC CGAGTTCGGG
1381 GACGAGCTGT CCTTCCGCGA GGGCGAGTCG GTCACCGTGC TGCGGAGGGA CGGGCCGGAG
1441 GAGACCGACT GGTGGTGGGC CGCGCTGCAC GGCCAGGAGG CTACGTGCC GCGGAACTAC
1501 TTCGGGCTGT CCCCAGGGT GAAGCCTCAA AGGAGTAAAG TCTAGCAGGA TAGAAGGAGG
1561 TTTCTGAGGC TGACAGAAAC AAGCATTCCT GCCTTCCCTC CAGACCTCTC CCTCTGTTTT
1621 TTGCTGCCTT TATCTGCACC CCTCACCCTG CTGGTGGTGG TCCTTGCCAC CGGTTCTCTG
1681 TTCTCCTGGA AGTCCAGGGA AGAAGGAGGG CCCCAGCCTT AAATTTAGTA ATCTGCCTTA
1741 GCCTTGGGAG GTCTGGGAAG GGCTGGAAAT CACTGGGGAC AGGAAACCAC TTCCTTTTGC
1801 CAAATCAGAT CCCGTCCAAA GTGCCTCCCA TGCCTACCAC CATCATCACA TCCCCCAGCA
1861 AGCCAGCCAC CTGCCCAGCC GGGCCTGGGA TGGGCCACCA CACCACTGGA TATTCCTGGG
1921 AGTCACTGCT GACACCATCT CTCCCAGCAG TCTTGGGGTC TGGGTGGGAA ACATTGGTCT
1981 CTACCAGGAT CCCTGCCCCA CCTCTCCCCA ATTAAGTGCC TTCACACAGC ACTGGTTTAA
2041 TGTTTATAAA CAAAATAGAG AAACTGGTTT AATGTTTATA AACAAAATAG AGAAACTTTC
2101 GCTTATAAAT AAAAGTAGTT TGCACAGAAA TGAAAAAAAA AAAAAAAAA AAAAA
```

Figure 1b

```
   1 atggtcacga ccagtagcgg aggggtata gggtacccgg caaacaacgg tgtcacacag
  61 gtgtctctga ttcactcgtc ggattctgta cgaactgttt caactgcccc aatataccgt
 121 ccgacgtcat caatggcatc tacgatggct cataaatctt cgacggctcc gttcatctcc
 181 gcaaatcaac gaatgtcaaa accgccggtt cgggtggtcg ctcaaccacc accaccacat
 241 ccacaagcat tgtcccaaca gtatcaccag cagaatccga tgatgatgta ttccgcacca
 301 aatacacgac cacacgttat tccgacaatg caagtgcaac cgacaatggc cgctcaaatt
 361 aaacgaaata atcctgttaa tgcacagttt cagaaccctt ctgaaatgat cgccgattac
 421 ggtgtaaaac cgcagtcagt agaaatggtg caaagagttc gagctgttcg aagacaagtc
 481 gccgacgagg agaccgaact gcgaagactc agagagcttg aacacgaaac ggcacagctt
 541 caaaataaga attatggaag agaaagagag ttgaatgtgc aaggatccat gctgaaagaa
 601 gctcaattag agttgagaaa tgcttcaatg agggcgcaat ctttaaacaa gcatttggaa
 661 gaaatgtacc ggagaagaca aactgcagca gcggcagcgc tgtggaaca acgaaaaatg
 721 cagcaacatc agattcttct agcccgagct gcaaatcaag tatccacaca agaagttata
 781 agacctcgtg cttctgtcga accattccaa gttaataata cccaacagca acaaccatca
 841 cctcaaatga tgaaatcaga agaattttcg gagaaagag atttgaatgg acaaactggc
 901 agttatgatg ctatcgatgg atcaggagat catcaaaaaa taccgacgga ccatcgtac
 961 ttggcaccat gtaaagaaaa ccagcaaaaa tactcggagt taagtaaaat ggcatctacg
1021 gatcctcatt caaatcacag ttcaccatca acttcttcgc agaaagctcc gacgttgatc
1081 acattttctc caccaagttt tgaacagaaa atcaactcgt ctacaatgac tcgggattct
1141 ccgttcgttg agcgtccaac atcgtttggt gatagtctag acgaatcacg actgagaagt
1201 ggaaagactg atttggtatc acttcgatca gattcctga aagctacgaa acgtcgttct
1261 tgggctgctt ccgaaggtac ttcaatgtca gaggcagaga tgattcatag gcttcttgat
1321 gaacaacgtc gtgggagatc acatttat ccacaattgc caacatcaca agaagaacca
1381 tcggcaataa catcagaaac atatgccgaa gaagttgtca attcagaatc gaaacaagtt
1441 gctacaagtt cggattccac taataatctt gaattgccaa ccgaacaaat ggtattaggt
1501 agtgatacca caacagaaga agatgcaagt tcgtgttcaa cacgttctga tgatggacag
1561 aatcttgaaa tggaagttgc gattgaaaga gaactgttaa aaggcatttt gagaagacct
1621 aatgaaaaga tgaacaaagg tcgcattgaa tttgacccat tagcactctt gctcgatgct
1681 gctttagaag gagaactcga tttagtgaga agcagtgcct caaagctaac agatgtctca
1741 caggccaatg atgaagggat tacggcgttg cacaatgcga tttgtgctgg acactatgag
1801 attgtaagat ttttgatcga gaacgacgct gatgtgaatg ctcaagattc cgatggttgg
1861 actccacttc attgtgcagc ttcctgtaat aaccttccaa tggttagaca acttgtggaa
1921 ggaggaggat gcgttctcgc ttcgacacta tctgtatatgg aaacacctgt ggagaagtgt
1981 gaagaagatg aagatggtta tgatggatgt tgaagtatc tttccgcagc cataactca
2041 acggatcaa ttaatactgg aaaagtttac gctgcttatg gatatgaggc ggcatttgaa
2101 gatgagctca gttttgatgc aggagatgaa ttgacgtta ttgagaaaga taaagtcgat
2161 aaaaattggt ggacatgtga gaagaacaat ggagagaagg gacaagtacc aagaacatat
2221 ttggcgttgt acccatcgtt aaaatacaga aagaagctca actttgtgat gttcgatctt
2281 ccattggaat cgaacaacaa tgtcgaataa
```

Figure 2a

MWMKDPVARPLSPTRLQPALPPEAQSVPELEEVARVLAEIPRPL

KRRGSMEQAPAVALPPTHKKQYQQIISRLFHRHGGPGPGGRSQSCPPSLRDLRPGQGP

LLLPHQLPFHRPAPSQSSPPEQPQSMEMRSVLRKAGSPRKARRARLNPLVLLLDAALT

GELEVVQQAVKEMNDPSQPNEEGITALHNAICGANYSIVDFLITAGANVNSPDSHGWT

PLHCAASCNDTVICMALVQHGAAIFATTLSDGATAFEKCDPYREGYADCATYLADVEQ

SMGLMNSGAVYALWDYSAEFGDELSFREGESVTVLRRDGPEETDWWWAALHGQEGYVP

RNYFGLFPRVKPQRSK

Figure 2b

```
                   MVTTSSGGGIGYPANNGVTQVSLIHSSDSVRTVSTAPIYRPTSS
MASTMAHKSSTAPFISANQRMSKPPVRVVAQPPPPHPQALSQQYHQQNPMMMYSAPNT
RPHVIPTMQVQPTMAAQIKRNNPVNAQFQNPSEMIADYGVKPQSVEMVQRVRAVRRQV
ADEETELRRLRELEHETAQLQNKNYGRERELNVQGSMLKEAQLELRNASMRAQSLNKH
LEEMYRRRQTAAAAALVEQRKMQQEQILLARAANQVSTQEVIRPRASVEPFQVNNTQQ
QQPSPQMMKSEEFSEKRDLNGQTGSYDAIDGSGDHQKIPTEPSYLAPCKENQQKYSEL
SKMASTDPHSNHSSPSTSSQKAPTLITFSPPSFEQKINSSTMTRDSPFVERPTSFGDS
LDESRLRSGKTDLVSLRSDSLKATKRRSWAASEGTSMSEAEMIHRLLDEQRRGRSHFI
PQLPTSQEEPSAITSETYAEEVVNSESKQVATSSDSTNNLELPTEQMVLGSDTTTEED
ASSCSTRSDDGQNLEMEVAIERRTVKGILRRPNEKMNKGRIEFDPLALLLDAALEGEL
DLVRSSASKLTDVSQANDEGITALHNAICAGHYEIVRFLIENDADVNAQDSDGWTPLH
CAASCNNLPMVRQLVEGGGCVLASTLSDMETPVEKCEEDEDGYDGCLKYLSAAHNSTG
SINTGKVYAAYGYEAAFEDELSFDAGDELTVIEKDKVDKNWWTCEKNNGEKGQVPRTY
LALYPSLKYRKKLNFVMFDLPLESNNNVE
```

Figure 6A
Figure 6B
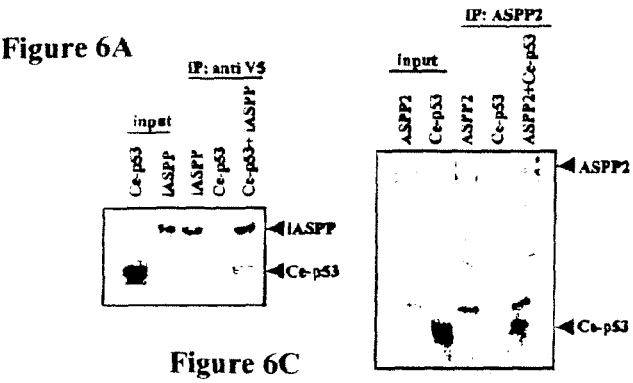
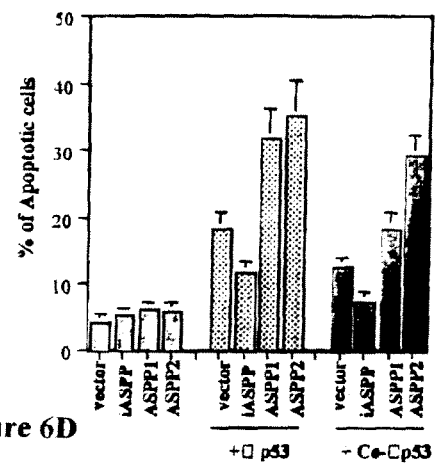
Figure 6C
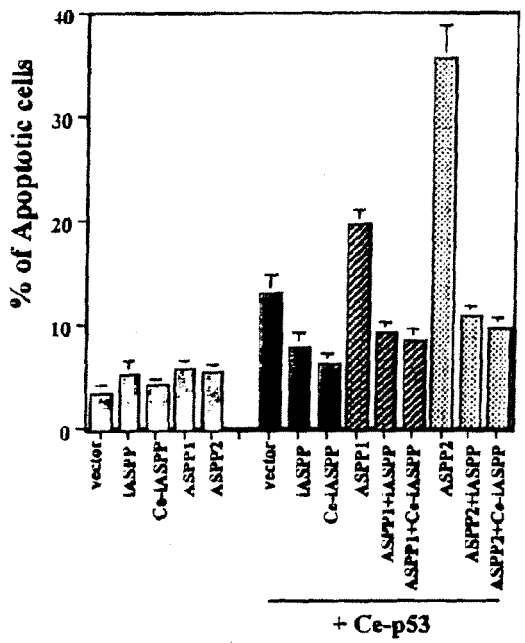
Figure 6D
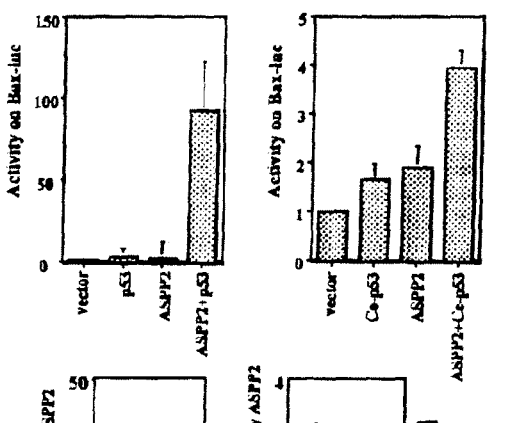
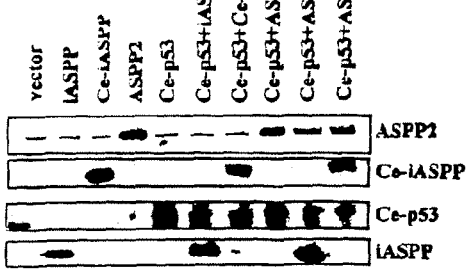
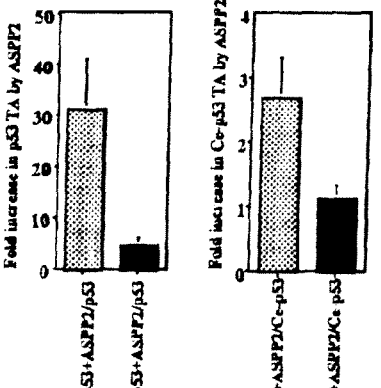
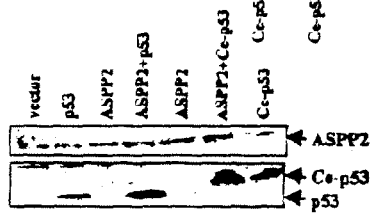

Figure 7

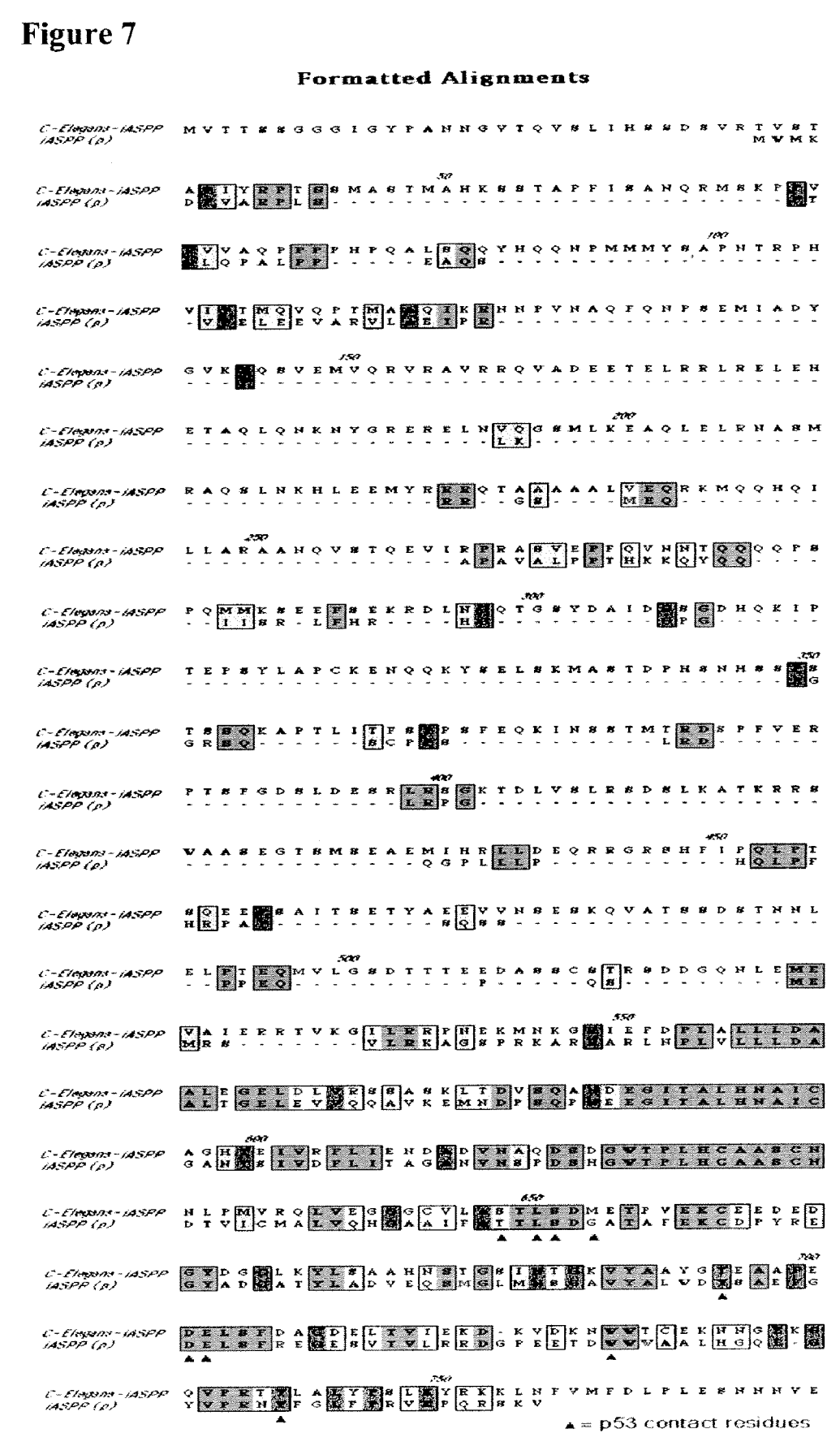

Formatted Alignments

[Sequence alignment of C-Elegans-iASPP and iASPP(p) proteins, approximately 750 residues. Highlighted positions indicate conserved or variant residues. Triangle markers (▲) below certain residues denote p53 contact residues.]

▲ = p53 contact residues

Figure 9A
*ape-1* = iASPP
*cep-1* = *Ce*-iASPP
Figure 9B
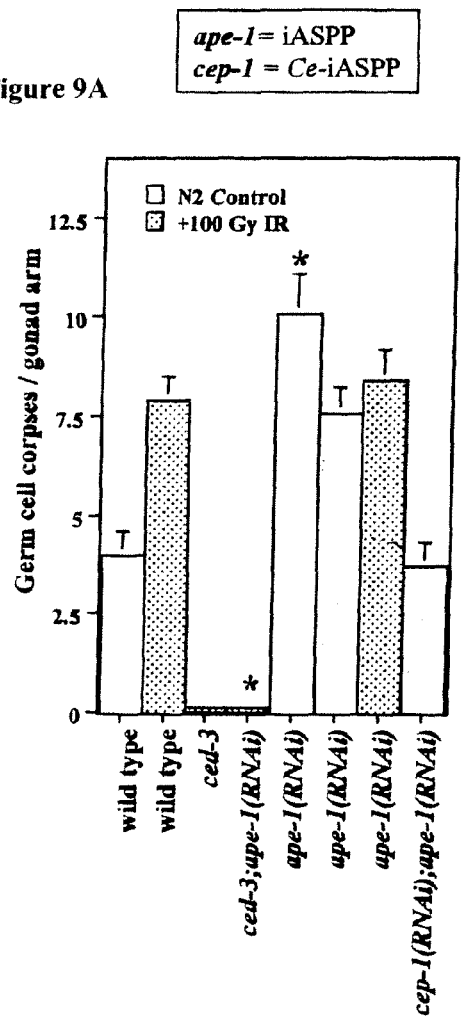
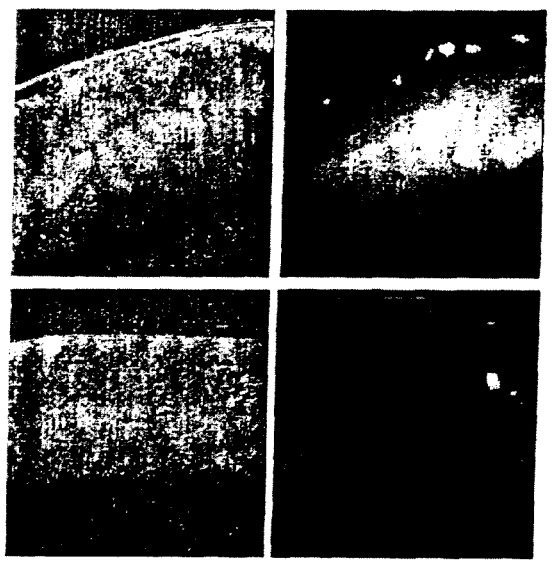

Figure 13
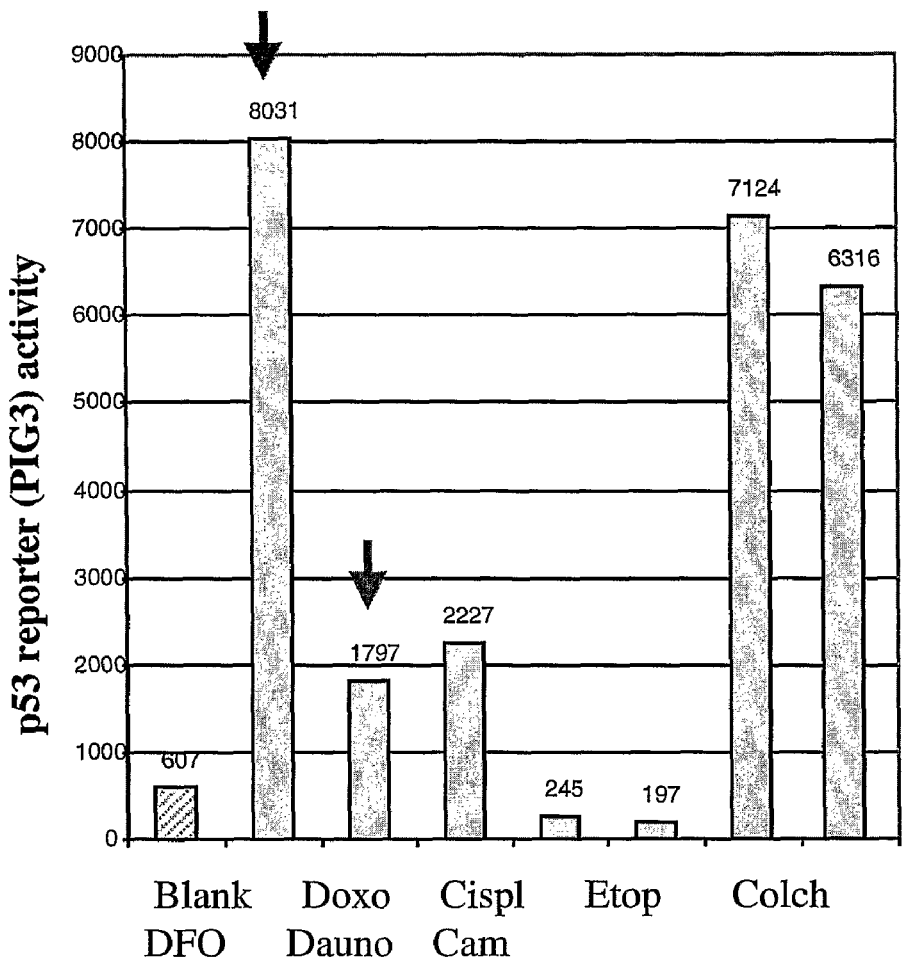
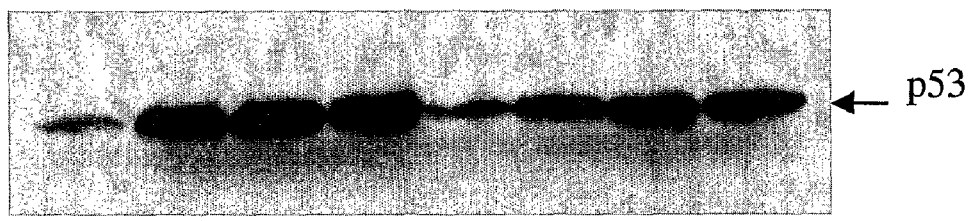
← p53
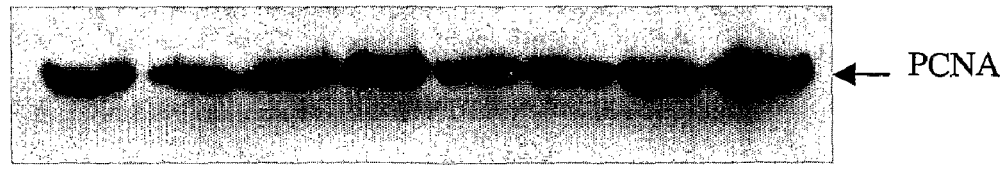
← PCNA

SEQUENCE LISTING

<160> NUMBER OF SEQ ID NOS: 9

<210> SEQ ID NO 1
<211> LENGTH: 6
<212> TYPE: PRT
<213> ORGANISM: Artificial sequence
<220> FEATURE:
<223> OTHER INFORMATION: p53 inhibitor peptide

```
<400> SEQUENCE: 1

Gly Pro Glu Glu Thr Asp
1               5

<210> SEQ ID NO 2
<211> LENGTH: 7
<212> TYPE: PRT
<213> ORGANISM: Artificial Sequence
<220> FEATURE:
<223> OTHER INFORMATION: p53 inhibitor peptide

<400> SEQUENCE: 2

Asp Gly Pro Glu Glu Thr Asp
1               5

<210> SEQ ID NO 3
<211> LENGTH: 6
<212> TYPE: PRT
<213> ORGANISM: Artificial Sequence
<220> FEATURE:
<223> OTHER INFORMATION: p53 inhibitor peptide

<400> SEQUENCE: 3

Thr Thr Leu Ser Asp Gly
1               5

<210> SEQ ID NO 4
<211> LENGTH: 6
<212> TYPE: PRT
<213> ORGANISM: Artificial Sequence
<220> FEATURE:
<223> OTHER INFORMATION: p53 inhibitor peptide

<400> SEQUENCE: 4

Pro Arg Asn Tyr Phe Gly
1               5

<210> SEQ ID NO 5
<211> LENGTH: 18
<212> TYPE: PRT
<213> ORGANISM: Artificial Sequence
<220> FEATURE:
<223> OTHER INFORMATION: p53 inhibitor peptide

<400> SEQUENCE: 5

Arg Leu Gln Pro Ala Leu Pro Pro Glu Ala Gln Ser Val Pro Glu Leu
1               5                   10                  15

Glu Glu

<210> SEQ ID NO 6
<211> LENGTH: 2156
<212> TYPE: DNA
<213> ORGANISM: Homo sapiens

<400> SEQUENCE: 6
gcggccgcgt cgacccggcg ttcagacgcg ggcagctacc ggcgctcgct gggctccgcg    60
gggccgtcgg gcactttgcc tcgcagctgg cagcccgtca gccgcatccc catgccccccc   120 tccagccccc agccccgcgg ggccccgcgc cagcgtccca tccccctcag catgatcttc   180
aagctgcaga acgccttctg ggagcacggg ccagccgcg ccatgctccc tgggtccccc   240
ctcttcaccc gagcaccccc gcctaagctg cagcccaac acaaccaca gcccagcca    300 caatcacaac cacagcccca gctgcccaa cagccccaga cccaacccca acccctacc    360
```

-continued

```
ccagcctccc acatccgcat ccccaacaga catggccccc tgtgaacgaa ggacccccca    420
aaccccccac cgagctggag cctgagccgg agatagaggg gctgctgaca ccagtgctgg    480
aggctggcga tgtggatgaa ggaccctgta gcaaggcctc tcagcccac gaggctgcag     540 ccagcactgc caccggaggc acagtcggtg cccgagctgg aggaggtggc acgggtgttg    600
gcggaaattc cccggcccct caaacgcagg ggctccatgg agcaggcccc tgctgtggcc    660
ctgcccccta cccacaagaa acagtaccag cagatcatca gccgcctctt ccatcgtcat    720 gggggggccag ggcccggggg gcggagccag agctgtcccc catcactgag ggatctgagg    780
ccagggcagg gcccctgct cctgccccac cagctcccat tccaccgccc ggccccgtcc     840
cagagcagcc caccagagca gccgcagagc atggagatgc gctctgtgct gcggaaggcg    900
ggctccccgc gcaaggcccg ccgcgcgcgc ctcaaccctc tggtgctcct cctggacgcg    960
gcgctgaccg gggagctgga ggtggtgcag caggcggtga aggagatgaa cgacccgagc    1020
cagcccaacg aggagggcat cactgccttg cacaacgcca tctgcggcgc caactactct    1080
atcgtggatt tcctcatcac cgcgggtgcc aatgtcaact ccccgacag ccacggctgg    1140 acacccttgc actgcgcggc gtcgtgcaac gacacagtca tctgcatggc gctggtgcag    1200 cacgcgctg caatcttcgc caccacgctc agcgacggcg ccaccgcctt cgagaagtgc    1260 gaccccttacc gcgagggtta tgctgactgc gccacctacc tggcagacgt cgagcagagt    1320
atggggctga tgaacagcgg ggcagtgtac gctctctggg actacagcgc cgagttcggg    1380
gacgagctgt ccttccgcga gggcgagtcg gtcaccgtgc tgcggaggga cgggccggag    1440
gagaccgact ggtggtgggc cgcgctgcac ggccaggagg gctacgtgcc gcggaactac    1500
ttcgggctgt tccccagggt gaagcctcaa aggagtaaag tctagcagga tagaaggagg    1560
tttctgaggc tgacagaaac aagcattcct gccttccctc cagacctctc cctctgtttt    1620
ttgctgcctt tatctgcacc cctcaccctg ctggtggtgg tccttgccac cggttctctg    1680
ttctcctgga agtccaggga agaaggaggg ccccagcctt aaatttagta atctgcctta    1740
gccttgggag gtctgggaag ggctggaaat cactggggac aggaaaccac ttccttttgc    1800
caaatcagat cccgtccaaa gtgcctccca tgcctaccac catcatcaca tcccccagca    1860
agccagccac ctgcccagcc gggcctggga tgggccacca caccactgga tattcctggg    1920
agtcactgct gacaccatct ctcccagcag tcttggggtc tgggtgggaa acattggtct    1980
ctaccaggat ccctgcccca cctctccca attaagtgcc ttcacacagc actggtttaa    2040
tgtttataaa caaaatagag aaactggttt aatgtttata acaaaatag agaaactttc    2100 gcttataaat aaaagtagtt tgcacagaaa tgaaaaaaaa aaaaaaaaa aaaaaa         2156
```

<210> SEQ ID NO 7
<211> LENGTH: 2310
<212> TYPE: DNA
<213> ORGANISM: Caenorhabditis elegans

<400> SEQUENCE: 7

```
atggtcacga ccagtagcgg agggggtata gggtacccgg caaacaacgg tgtcacacag     60
gtgtctctga ttcactcgtc ggattctgta cgaactgttt caactgcccc aatataccgt    120
ccgacgtcat caatggcatc tacgatggct cataaatctt cgacggctcc gttcatctcc    180
gcaaatcaac gaatgtcaaa accgccggtt cgggtggtcg ctcaaccacc accaccacat    240
ccacaagcat tgtcccaaca gtatcaccag cagaatccga tgatgatgta ttccgcacca    300
```

| | | | | |
|---|---|---|---|---|
| aatacacgac | cacacgttat | tccgacaatg | caagtgcaac | cgacaatggc cgctcaaatt | 360 |
| aaacgaaata | atcctgttaa | tgcacagttt | cagaacccct | ctgaaatgat cgccgattac | 420 |
| ggtgtaaaac | cgcagtcagt | agaaatggtg | caaagagttc | gagctgttcg aagacaagtc | 480 |
| gccgacgagg | agaccgaact | gcgaagactc | agagagcttg | aacacgaaac ggcacagctt | 540 |
| caaaataaga | attatggaag | agaaagagag | ttgaatgtgc | aaggatccat gctgaaagaa | 600 |
| gctcaattag | agttgagaaa | tgcttcaatg | agggcgcaat | cttttaaacaa gcatttggaa | 660 |
| gaaatgtacc | ggagaagaca | aactgcagca | gcggcagcgc | tcgtggaaca acgaaaaatg | 720 |
| cagcaacatc | agattcttct | agcccgagct | gcaaatcaag | tatccacaca agaagttata | 780 |
| agacctcgtg | cttctgtcga | accattccaa | gttaataata | cccaacagca acaaccatca | 840 |
| cctcaaatga | tgaaatcaga | agaattttcg | gagaaaagag | atttgaatgg acaaactggc | 900 |
| agttatgatg | ctatcgatgg | atcaggagat | catcaaaaaa | taccgacgga gccatcgtac | 960 |
| ttggcaccat | gtaaagaaaa | ccagcaaaaa | tactcggagt | taagtaaaat ggcatctacg | 1020 |
| gatcctcatt | caaatcacag | ttcaccatca | acttcttcgc | agaaagctcc gacgttgatc | 1080 |
| acattttctc | caccaagttt | tgaacagaaa | atcaactcgt | ctacaatgac tcgggattct | 1140 |
| ccgttcgttg | agcgtccaac | atcgtttggt | gatagtctag | acgaatcacg actgagaagt | 1200 |
| ggaaagactg | atttggtatc | acttcgatca | gattccctga | agctacgaa acgtcgttct | 1260 |
| tgggctgctt | ccgaaggtac | ttcaatgtca | gaggcagaga | tgattcatag gcttcttgat | 1320 |
| gaacaacgtc | gtgggagatc | acattttatt | ccacaattgc | caacatcaca agaagaacca | 1380 |
| tcggcaataa | catcagaaac | atatgccgaa | gaagttgtca | attcagaatc gaaacaagtt | 1440 |
| gctacaagtt | cggattccac | taataatctt | gaattgccaa | ccgaacaaat ggtattaggt | 1500 |
| agtgatacca | acagaagaga | agatgcaagt | tcgtgttcaa | cacgttctga tgatggacag | 1560 |
| aatcttgaaa | tggaagttgc | gattgaaaga | agaactgtta | aaggcatttt gagaagacct | 1620 |
| aatgaaaaga | tgaacaaagg | tcgcattgaa | tttgacccat | tagcactctt gctcgatgct | 1680 |
| gctttagaag | gagaactcga | tttagtgaga | agcagtgcct | caaagctaac agatgtctca | 1740 |
| caggccaatg | atgaagggat | tacggcgttg | cacaatgcga | tttgtgctgg acactatgag | 1800 |
| attgtaagat | ttttgatcga | gaacgacgct | gatgtgaatg | ctcaagattc cgatggttgg | 1860 |
| actccacttc | attgtgcagc | ttcctgtaat | aaccttccaa | tggttagaca acttgtggaa | 1920 |
| ggaggaggat | gcgttctcgc | ttcgacacta | tctgatatgg | aaacacctgt ggagaagtgt | 1980 |
| gaagaagatg | aagatggtta | tgatggatgt | ttgaagtatc | tttccgcagc ccataactca | 2040 |
| acgggatcaa | ttaatactgg | aaaagtttac | gctgcttatg | gatatgaggc ggcatttgaa | 2100 |
| gatgagctca | gttttgatgc | aggagatgaa | ttgacggtta | ttgagaaaga taaagtcgat | 2160 |
| aaaaattggt | ggacatgtga | gaagaacaat | ggagagaagg | gacaagtacc aagaacatat | 2220 |
| ttggcgttgt | acccatcgtt | aaaatacaga | agaagctca | actttgtgat gttcgatctt | 2280 |
| ccattggaat | cgaacaacaa | tgtcgaataa | | | 2310 |

<210> SEQ ID NO 8
<211> LENGTH: 350
<212> TYPE: PRT
<213> ORGANISM: Homo sapiens

<400> SEQUENCE: 8

Met Trp Met Lys Asp Pro Val Ala Arg Pro Leu Ser Pro Thr Arg Leu
1               5                   10                  15

```
Gln Pro Ala Leu Pro Pro Glu Ala Gln Ser Val Pro Glu Leu Glu Glu
            20                  25                  30

Val Ala Arg Val Leu Ala Glu Ile Pro Arg Pro Leu Lys Arg Arg Gly
        35                  40                  45

Ser Met Glu Gln Ala Pro Ala Val Ala Leu Pro Thr His Lys Lys
    50                  55                  60

Gln Tyr Gln Gln Ile Ile Ser Arg Leu Phe His Arg His Gly Gly Pro
65                  70                  75                  80

Gly Pro Gly Gly Arg Ser Gln Ser Cys Pro Pro Ser Leu Arg Asp Leu
                85                  90                  95

Arg Pro Gly Gln Gly Pro Leu Leu Pro His Gln Leu Pro Phe His
        100                 105                 110

Arg Pro Ala Pro Ser Gln Ser Ser Pro Pro Glu Gln Pro Gln Ser Met
            115                 120                 125

Glu Met Arg Ser Val Leu Arg Lys Ala Gly Ser Pro Arg Lys Ala Arg
    130                 135                 140

Arg Ala Arg Leu Asn Pro Leu Val Leu Leu Asp Ala Ala Leu Thr
145                 150                 155                 160

Gly Glu Leu Glu Val Val Gln Gln Ala Val Lys Glu Met Asn Asp Pro
                165                 170                 175

Ser Gln Pro Asn Glu Glu Gly Ile Thr Ala Leu His Asn Ala Ile Cys
            180                 185                 190

Gly Ala Asn Tyr Ser Ile Val Asp Phe Leu Ile Thr Ala Gly Ala Asn
        195                 200                 205

Val Asn Ser Pro Asp Ser His Gly Trp Thr Pro Leu His Cys Ala Ala
    210                 215                 220

Ser Cys Asn Asp Thr Val Ile Cys Met Ala Leu Val Gln His Gly Ala
225                 230                 235                 240

Ala Ile Phe Ala Thr Thr Leu Ser Asp Gly Ala Thr Ala Phe Glu Lys
                245                 250                 255

Cys Asp Pro Tyr Arg Glu Gly Tyr Ala Asp Cys Ala Thr Tyr Leu Ala
            260                 265                 270

Asp Val Glu Gln Ser Met Gly Leu Met Asn Ser Gly Ala Val Tyr Ala
        275                 280                 285

Leu Trp Asp Tyr Ser Ala Glu Phe Gly Asp Glu Leu Ser Phe Arg Glu
    290                 295                 300

Gly Glu Ser Val Thr Val Leu Arg Arg Asp Gly Pro Glu Glu Thr Asp
305                 310                 315                 320

Trp Trp Trp Ala Ala Leu His Gly Gln Glu Gly Tyr Val Pro Arg Asn
                325                 330                 335

Tyr Phe Gly Leu Phe Pro Arg Val Lys Pro Gln Arg Ser Lys
            340                 345                 350

<210> SEQ ID NO 9
<211> LENGTH: 769
<212> TYPE: PRT
<213> ORGANISM: Caenorhabditis elegans

<400> SEQUENCE: 9

Met Val Thr Thr Ser Gly Gly Gly Ile Gly Tyr Pro Ala Asn Asn
1               5                   10                  15

Gly Val Thr Gln Val Ser Leu Ile His Ser Ser Asp Ser Val Arg Thr
            20                  25                  30

Val Ser Thr Ala Pro Ile Tyr Arg Pro Thr Ser Ser Met Ala Ser Thr
        35                  40                  45
```

```
Met Ala His Lys Ser Ser Thr Ala Pro Phe Ile Ser Ala Asn Gln Arg
         50                  55                  60
Met Ser Lys Pro Pro Val Arg Val Val Ala Gln Pro Pro Pro Pro His
 65                  70                  75                  80
Pro Gln Ala Leu Ser Gln Gln Tyr His Gln Asn Pro Met Met Met
                 85                  90                  95
Tyr Ser Ala Pro Asn Thr Arg Pro His Val Ile Pro Thr Met Gln Val
             100                 105                 110
Gln Pro Thr Met Ala Ala Gln Ile Lys Arg Asn Asn Pro Val Asn Ala
             115                 120                 125
Gln Phe Gln Asn Pro Ser Glu Met Ile Ala Asp Tyr Gly Val Lys Pro
         130                 135                 140
Gln Ser Val Glu Met Val Gln Arg Val Arg Ala Val Arg Arg Gln Val
145                 150                 155                 160
Ala Asp Glu Glu Thr Glu Leu Arg Arg Leu Arg Glu Leu His Glu
                 165                 170                 175
Thr Ala Gln Leu Gln Asn Lys Asn Tyr Gly Arg Glu Arg Glu Leu Asn
             180                 185                 190
Val Gln Gly Ser Met Leu Lys Glu Ala Gln Leu Glu Leu Arg Asn Ala
         195                 200                 205
Ser Met Arg Ala Gln Ser Leu Asn Lys His Leu Glu Glu Met Tyr Arg
    210                 215                 220
Arg Arg Gln Thr Ala Ala Ala Ala Leu Val Glu Gln Arg Lys Met
225                 230                 235                 240
Gln Gln His Gln Ile Leu Leu Ala Arg Ala Ala Asn Gln Val Ser Thr
                 245                 250                 255
Gln Glu Val Ile Arg Pro Arg Ala Ser Val Glu Pro Phe Gln Val Asn
             260                 265                 270
Asn Thr Gln Gln Gln Pro Ser Pro Gln Met Met Lys Ser Glu Glu
         275                 280                 285
Phe Ser Glu Lys Arg Asp Leu Asn Gly Gln Thr Gly Ser Tyr Asp Ala
    290                 295                 300
Ile Asp Gly Ser Gly Asp His Gln Lys Ile Pro Thr Glu Pro Ser Tyr
305                 310                 315                 320
Leu Ala Pro Cys Lys Glu Asn Gln Gln Lys Tyr Ser Glu Leu Ser Lys
                 325                 330                 335
Met Ala Ser Thr Asp Pro His Ser Asn His Ser Ser Pro Ser Thr Ser
             340                 345                 350
Ser Gln Lys Ala Pro Thr Leu Ile Thr Phe Ser Pro Pro Ser Phe Glu
         355                 360                 365
Gln Lys Ile Asn Ser Ser Thr Met Thr Arg Asp Ser Pro Phe Val Glu
    370                 375                 380
Arg Pro Thr Ser Phe Gly Asp Ser Leu Asp Glu Ser Arg Leu Arg Ser
385                 390                 395                 400
Gly Lys Thr Asp Leu Val Ser Leu Arg Ser Asp Ser Leu Lys Ala Thr
             405                 410                 415
Lys Arg Arg Ser Trp Ala Ala Ser Glu Gly Thr Ser Met Ser Glu Ala
         420                 425                 430
Glu Met Ile His Arg Leu Leu Asp Glu Gln Arg Gly Arg Ser His
             435                 440                 445
Phe Ile Pro Gln Leu Pro Thr Ser Gln Glu Glu Pro Ser Ala Ile Thr
    450                 455                 460
```

-continued

```
Ser Glu Thr Tyr Ala Glu Val Val Asn Ser Glu Ser Lys Gln Val
465                 470                 475                 480

Ala Thr Ser Ser Asp Ser Thr Asn Asn Leu Glu Leu Pro Thr Glu Gln
                485                 490                 495

Met Val Leu Gly Ser Asp Thr Thr Glu Glu Asp Ala Ser Ser Cys
            500                 505                 510

Ser Thr Arg Ser Asp Asp Gly Gln Asn Leu Glu Met Glu Val Ala Ile
            515                 520                 525

Glu Arg Arg Thr Val Lys Gly Ile Leu Arg Arg Pro Asn Glu Lys Met
    530                 535                 540

Asn Lys Gly Arg Ile Glu Phe Asp Pro Leu Ala Leu Leu Leu Asp Ala
545                 550                 555                 560

Ala Leu Glu Gly Glu Leu Asp Leu Val Arg Ser Ser Ala Ser Lys Leu
                565                 570                 575

Thr Asp Val Ser Gln Ala Asn Asp Glu Gly Ile Thr Ala Leu His Asn
            580                 585                 590

Ala Ile Cys Ala Gly His Tyr Glu Ile Val Arg Phe Leu Ile Glu Asn
        595                 600                 605

Asp Ala Asp Val Asn Ala Gln Asp Ser Asp Gly Trp Thr Pro Leu His
    610                 615                 620

Cys Ala Ala Ser Cys Asn Asn Leu Pro Met Val Arg Gln Leu Val Glu
625                 630                 635                 640

Gly Gly Gly Cys Val Leu Ala Ser Thr Leu Ser Asp Met Glu Thr Pro
            645                 650                 655

Val Glu Lys Cys Glu Glu Asp Glu Asp Gly Tyr Asp Gly Cys Leu Lys
            660                 665                 670

Tyr Leu Ser Ala Ala His Asn Ser Thr Gly Ser Ile Asn Thr Gly Lys
        675                 680                 685

Val Tyr Ala Ala Tyr Gly Tyr Glu Ala Ala Phe Glu Asp Glu Leu Ser
    690                 695                 700

Phe Asp Ala Gly Asp Glu Leu Thr Val Ile Glu Lys Asp Lys Val Asp
705                 710                 715                 720

Lys Asn Trp Trp Thr Cys Glu Lys Asn Asn Gly Glu Lys Gly Gln Val
                725                 730                 735

Pro Arg Thr Tyr Leu Ala Leu Tyr Pro Ser Leu Lys Tyr Arg Lys Lys
            740                 745                 750

Leu Asn Phe Val Met Phe Asp Leu Pro Leu Glu Ser Asn Asn Asn Val
            755                 760                 765

Glu
```

PEPTIDE INHIBITORS OF IASPP

This application is a divisional of U.S. patent application Ser. No. 10/522,043, filed Oct. 13, 2005, incorporated herein by reference in its entirety, which is a §371 National Phase of International Application No. PCT/GB2003/004296, filed Oct. 3, 2003, which claims priority benefit of each of the following Great Britain Applications: Application No. 0306261.9 filed Mar. 19, 2003, and Application No. 0223193.4 filed Oct. 7, 2002.

The invention relates to a polypeptide, or part thereof, which inhibits the apoptotic activity of the tumour suppressor protein p53; screening methods to identify agents which interfere with the activity of said polypeptide and agents with said activity.

Apoptosis, or programmed cell death, is a process by which multi-cellular organisms regulate cell number and differentiation. The process is regulated by factors which either induce or prevent apoptosis. Inducers of apoptosis include Bcl-2 family members, caspase family members and their associated factors Apaf-1 and Fadd. Caspases are synthesised as proenzymes which become activated after proteolytic cleavage. The active caspase then induces many of the morphological and biochemical changes associated with apoptosis. Mitochondria play a pivotal role in the activation process through the release of pro-apoptotic factors such as cytochrome c, AIF and Diablo. The release from mitochondria is controlled by the Bcl-2 family of proteins; (e.g. Bcl-2 and Bcl-x1 inhibit release; Bax and Bak induce release).

WO9953051 discloses a cytokine dependent protein p21 which has pro-apoptotic activity. p21 is expressed in a cytokine dependent manner in myeloid/erthyroid cells. These cells are dependent on IL-3 for growth and in the absence of IL-3 the translation of p21 is induced resulting in apoptosis and cell death. p21 is a cytoplasmic protein which translocates to the outer mitochondrial membrane to induce pro-apoptotic activities.

Tumour suppressor proteins also have pro-apoptotic activities.

Tumour suppressor genes encode proteins which function to inhibit cell growth or division and are therefore important with respect to maintaining proliferation, growth and differentiation of normal cells. Mutations in tumour suppressor genes result in abnormal cell-cycle progression whereby the normal cell-cycle check points which arrest the cell-cycle, when, for example, DNA is damaged, are ignored and damaged cells divide uncontrollably. The products of tumour suppressor genes function in all parts of the cell (e.g. cell surface, cytoplasm, nucleus) to prevent the passage of damaged cells through the cell-cycle (i.e. G1, S, G2, M and cytokinesis).

Arguably the tumour suppressor gene which has been the subject of the most intense research is p53. p53 encodes a protein which functions as a transcription factor and is a key regulator of the cell division cycle. It was discovered in 1978 as a protein shown to bind with affinity to the SV40 large T antigen. The p53 gene encodes a 393 amino acid polypeptide with a molecular weight of 53 kDa. Genes regulated by the transcriptional activity of p53 contain a p53 recognition sequence in their 5' regions. These genes are activated when the cellular levels of p53 are elevated due to, for example DNA damage. Examples of genes which respond to p53 include, mdm2, Bax and PIG-3. Bax and PIG-3 are involved in one of the most important functions of p53, the induction of apoptosis.

In our co-pending application WO02/12325 we disclose a family of proteins, referred to as ASPP, as specific activators of p53 and revealed a mechanism by which wild type p53 is tolerated in tumours, such as human breast carcinomas. We also disclose an inhibitor of ASPP family members referred to as iASPP. iASPP is an oncogene and is the most conserved member of the ASPP family. iASPP is the only ASPP-like protein found in *C. elegans*. Similar to human iASPP, the *C. elegans* homologue functions as a key inhibitor of p53. These findings indicate that regulation of p53 function by members of the ASPP family has been evolutionarily conserved across phyla.

The *C. elegans* iASPP is capable of substituting for human iASPP in all of the assays performed in human cells. Moreover, reciprocal substitution studies reveal that the apoptotic function of *C. elegans* p53 is enhanced or inhibited by human ASPP and iASPP, respectively. Using RNAi we further demonstrate that iASPP is a key inhibitor of p53 mediated apoptosis in *C. elegans*. All of these observations show that the regulation of p53 by ASPP family members is evolutionarily conserved. Control of p53 activity plays a pivotal role in development and tumourigenesis. Hence, inhibiting the oncogenic function of iASPP could provide an important new strategy for treating tumours expressing wild type p53. Sequence comparison between *C. elegans* and human iASPP reveals a conserved domain between the nematode and human sequence which likely explains the functional conservation between the proteins.

According to an aspect of the invention there is provided an isolated nucleic acid molecule which encodes a polypeptide, or sequence variant thereof, wherein said polypeptide is a fragment of the polypeptide sequence represented in FIG. 1*a* or 1*b*, which fragment is selected from the group consisting of:

i) a polypeptide fragment consisting of amino acid residues from about residue 128-224 of the amino acid sequence presented in FIG. 1*a* or 1*b*;

ii) a polypeptide fragment consisting of amino acid residues from about 128-244 of the amino acid sequence presented in FIG. 1*a* or 1*b* wherein said sequence has been modified by addition, deletion or substitution of at least one amino acid residue; and iii) a polypeptide as defined in (i) and (ii) wherein said polypeptide substantially retains the biological activity of the polypeptide represented in FIG. 1*a* or 1*b*.

In a preferred embodiment of the invention said nucleic acid molecule encodes a polypeptide fragment consisting of amino acid residues from about 128-224 of the sequence represented in FIG. 1*a*. Preferably said nucleic acid molecule is isolated from a human.

In an alternative preferred embodiment of the invention said nucleic acid molecule encodes a polypeptide fragment consisting of amino acid residues from about 128-224 of the sequence represented in FIG. 1*b*. Preferably said nucleic acid molecule is isolated from a nematode. Preferably said nematode is of the genus *Caenorhabditis* spp.

In a preferred embodiment of the invention said nucleic acid molecule encodes a polypeptide, or sequence variant thereof, which polypeptide inhibits the activity of a polypeptide represented by the amino acid sequence represented in FIG. 1*a* or 1*b*.

In a preferred embodiment of the invention said nucleic acid molecule is a cDNA.

In an alternative preferred embodiment of the invention said nucleic acid molecule is genomic DNA.

According to a further aspect of the invention there is provided a polypeptide fragment or sequence variant thereof, encoded by a nucleic acid molecule according to the invention.

It will be apparent that fragments which are sequence variants may retain the biological activity of the full length polypeptide or alternatively have antagonistic activity by competing for binding sites in p53. In general, the specificity of polypeptides according to the invention with respect to binding to p53 is shown by binding equilibrium constants. Polypeptides which are capable of selectively binding p53 preferably have binding equilibrium constants of at least about $10^7$ $M^{-1}$, more preferably at least about $10^8$ $M^{-1}$, and most preferably at least about $10^9$ $M^{-1}$.

A sequence variant, i.e. a fragment polypeptide and reference polypeptide may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalaine, tyrosine and tryptophan.

A functionally equivalent polypeptide according to the invention is a variant wherein one or more amino acid residues are substituted with conserved or non-conserved amino acid residues, or one in which one or more amino acid residues includes a substituent group. Conservative substitutions are the replacements, one for another, among the aliphatic amino acids Ala, Val, Leu and Ile; interchange of the hydroxl residues Ser and Thr; exchange of the acidic residues Asp and Glu; substitution between amide residues Asn and Gln; exchange of the basic residues Lys and Arg; and replacements among aromatic residues Phe and Tyr.

In addition, the invention features polypeptide sequences having at least 75% identity with the polypeptide sequences as herein disclosed, or fragments and functionally equivalent polypeptides thereof. In one embodiment, the polypeptides have at least 85% identity, more preferably at least 90% identity, even more preferably at least 95% identity, still more preferably at least 97% identity, and most preferably at least 99% identity with the amino acid sequences illustrated herein.

As mentioned above, the invention also provides, in certain embodiments, "dominant negative" polypeptides derived from the polypeptides herein disclosed. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to another transcription factor or to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, given the teachings contained herein of iASPP polypeptides, one of ordinary skill in the art can modify the sequence of iASPP polypeptides by site-specific mutagenesis, scanning mutagenesis, partial gene deletion or truncation, and the like. See, e.g., U.S. Pat. No. 5,580,723 and Sambrook et al., Molecular Cloning: A Laboratory Manual, Second Edition, Cold Spring Harbor Laboratory Press, 1989. The skilled artisan then can test the population of mutagenized polypeptides for diminution in a selected activity (e.g., p53 binding, modulation of apoptosis) and/or for retention of such an activity. Other similar methods for creating and testing dominant negative variants of a protein will be apparent to one of ordinary skill in the art.

According to a further aspect of the invention there is provided a vector comprising a nucleic acid according to the invention.

In a further preferred method of the invention said vector is an expression vector conventionally adapted for gene expression.

Typically said adaptation includes, by example and not by way of limitation, the provision of transcription control sequences (promoter sequences) which mediate cell/tissue specific expression. These promoter sequences may be cell/tissue specific, inducible or constitutive.

Promoter is an art recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences and is therefore position independent). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors (please see Eukaryotic Transcription Factors, by David S Latchman, Academic Press Ltd, San Diego) is responsive to a number of environmental cues which include, by example and not by way of limitation, intermediary metabolites (eg glucose, lipids), environmental effectors (eg light, heat).

Promoter elements also include so called TATA box and RNA polymerase initiation selection (RIS) sequences which function to select a site of transcription initiation. These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell or prokaryotic host. Vectors which are maintained autonomously are referred to as episomal vectors. Episomal vectors are desirable since these molecules can incorporate large DNA fragments (30-50 kb DNA). Episomal vectors of this type are described in WO98/07876.

Adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

Expression control sequences also include so-called Locus Control Regions (LCRs). These are regulatory elements which confer position-independent, copy number-dependent expression to linked genes when assayed as transgenic constructs in mice. LCRs include regulatory elements that insulate transgenes from the silencing effects of adjacent heterochromatin, Grosveld et al., Cell (1987), 51: 975-985.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

According to a further aspect of the invention there is provided a cell transformed or transfected with a nucleic acid molecule or vector according to the invention.

Preferably, said host cells are eukaryotic cells, for example, insect cells such as cells from a species *Spodoptera frugiperda* using a baculovirus expression system. This expression system is favoured in the instance where post-translational modification of the polypeptide is required. Host cells and cell lines, can be prokaryotic (e.g., *E. coli*), or eukaryotic (e.g., CHO cells, COS cells, yeast expression systems and recombinant baculovirus expression in insect cells). Especially useful are mammalian cells such as human, mouse, hamster, pig, goat, primate, etc. They may be of a wide variety of tissue types, and include primary cells and cell lines. Specific examples include keratinocytes, peripheral blood leukocytes, fibroblasts, bone marrow stem cells and embryonic stem cells. The expression vectors require that the pertinent sequence, i.e., those nucleic acids described above, be operably linked to a promoter.

According to a further aspect of the invention the invention there is provided a polypeptide according to the invention for use as a pharmaceutical.

According to a further aspect of the invention there is provided a nucleic acid according to the invention for use as a pharmaceutical.

In a preferred embodiment of the invention said pharmaceutical further comprises a diluent, carrier or excipient.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents, such as chemotherapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp 1694-1712; incorporated by reference). Those of skill in the art can readily determine the various parameters and conditions for producing antibody aerosols without resort to undue experimentation. When using antisense preparations of the invention, slow intravenous administration is preferred.

The compositions of the invention are administered in effective amounts. An "effective amount" is that amount of a composition that alone, or together with further doses, produces the desired response. In the case of treating a particular disease, such as cancer, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of dominant negative iASPP or nucleic acid encoding a dominant negative iASPP, for producing the desired response in a unit of weight or volume suitable for administration to a patient. The response can, for example, be measured by determining the signal transduction inhibited by the dominant negative iASPP-1, composition via a reporter system as described herein, by measuring downstream effects such as gene expression, or by measuring the physiological effects of the iASPP composition, such as regression of a tumour, decrease of disease symptoms, modulation of apoptosis, etc.

The doses of dominant negative iASPP polypeptide or nucleic acid administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses of dominant negative iASPP are formulated and administered in doses between 1 ng and about 500 mg, and between 10 ng and 100 mg, according to any standard procedure in the art. Where nucleic acids encoding dominant negative iASPP are employed, doses of between 1 ng and 0.1 mg generally will be formulated and administered according to standard procedures. Other protocols for the administration of iASPP compositions will be known to one of ordinary skill in the art, in which the dose amount, schedule of injections, sites of injections, mode of administration (e.g., intratumoral) and the like vary from the foregoing. Administration of iASPP compositions to mammals other than humans, e.g. for testing purposes or veterinary therapeutic purposes, is carried out under substantially the same conditions as described above. A subject, as used herein, is a mammal, preferably a human, and including a non-human primate, cow, horse, pig, sheep, goat, dog, cat or rodent.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

iASPP compositions may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous or non-aqueous preparation of iASPP polypeptides or nucleic acids, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

According to a further aspect of the invention there is provided a transgenic non-human animal comprising a nucleic acid according to the invention.

The invention also includes transgenic non-human animals. As used herein, "transgenic non-human animals" includes non-human animals having one or more exogenous nucleic acid molecules incorporated in germ line cells and/or somatic cells. Thus the transgenic animal include "knockout" animals having a homozygous or heterozygous gene disruption by homologous recombination, animals having episomal or chromosomally incorporated expression vectors, etc. Knockout animals can be prepared by homologous recombination using embryonic stem cells as is well known in the art. The recombination can be facilitated by the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to iASPP family nucleic acid molecules to increase expression of these nucleic acid molecules in a regulated or conditional manner. Trans-acting negative regulators of iASPP activity or expression also can be operably linked to a conditional promoter as described above. Such trans-acting regulators include antisense nucleic acids molecules, nucleic acid molecules which encode dominant negative molecules, ribozyme molecules specific for iASPP nucleic acids, and the like. The transgenic non-human animals are useful in experiments directed toward testing biochemical or physiological effects of diagnostics or therapeutics for conditions characterized by increased or decrease iASPP expression. Other uses will be apparent to one of ordinary skill in the art.

According to a further aspect of the invention there is provided the use of the polypeptide, or fragment thereof, in a screening method for the identification of agents which inhibit the binding of said polypeptide to p53.

According to a further aspect of the invention there is provided a screening method to identify agents which inhibit the binding of a polypeptide or fragment thereof to p53 comprising:
   i) forming a preparation comprising
      a) a polypeptide according to the invention; and
      b) a p53 polypeptide, or a fragment thereof consisting of the binding site(s) for the polypeptide in (a);
   ii) providing at least one agent to be tested; and
   iii) determining the activity of the agent with respect to the binding of the polypeptide in (a) to the polypeptide in (b).

In a preferred method of the invention said agent is a polypeptide, preferably a peptide.

In a preferred method of the invention said peptide comprises an amino acid sequence selected from the group consisting of: GPEETD (SEQ ID NO: 1); DGPEETD (SEQ ID NO: 2); TTLSDG (SEQ ID NO: 3); AEFGDE (SEQ ID NO: 8, amino acids 294-299); or PRNYFG (SEQ ID NO: 4).

In a preferred method of the invention said peptide is at least 6 amino acid residues in length. Preferably the length of said peptide is selected from the group consisting of: at least 7 amino acid residues; 8, 9, 10, 11, 12, 13, 14, 15, 16, 17, 18, 19, or 20 amino acid residues in length. Alternatively the length of said peptide is at least 20 amino acid residues; 30; 40; 50; 60; 70; 80; 90; or 100 amino acid residues in length.

In a further preferred method of the invention said peptide consists of an amino acid sequence consisting of: GPEETD (SEQ ID NO: 1); DGPEETD (SEQ ID NO: 2); TTLSDG (SEQ ID NO: 3); AEFGDE (SEQ ID NO: 8, amino acids 294-299); or PRNYFG (SEQ ID NO: 4).

It will be apparent to one skilled in the art that modification to the amino acid sequence of peptides agents could enhance the binding and/or stability of the peptide with respect to its target sequence. In addition, modification of the peptide may also increase the in vivo stability of the peptide thereby reducing the effective amount of peptide necessary to inhibit p53 binding of iASPP. This would advantageously reduce undesirable side effects which may result in vivo. Modifications include, by example and not by way of limitation, acetylation and amidation. Alternatively or preferably, said modification includes the use of modified amino acids in the production of recombinant or synthetic forms of peptides. It will be apparent to one skilled in the art that modified amino acids include, by way of example and not by way of limitation, 4-hydroxyproline, 5-hydroxylysine, $N^6$-acetyllysine, $N^6$-methyllysine, $N^6,N^6$-dimethyllysine, $N^6,N^6,N^6$-trimethyllysine, cyclohexyalanine, D-amino acids, onithine. Other modifications include amino acids with a $C_2$, $C_3$ or $C_4$ alkyl R group optionally substituted by 1, 2 or 3 substituents selected from halo (eg F, Br, I), hydroxy or $C_1$-$C_4$ alkoxy.

It will also be apparent to one skilled in the art that peptides which retain p53 binding activity could be modified by cyclisation. Cyclisation is known in the art, (see Scott et al Chem Biol (2001), 8:801-815; Gellerman et al J. Peptide Res (2001), 57: 277-291; Dutta et al J. Peptide Res (2000), 8: 398-412; Ngoka and Gross J Amer Soc Mass Spec (1999), 10:360-363.

In a further preferred method of the invention said antagonist is an antibody or antibody binding part. Preferably said antibody is a monoclonal antibody or binding part thereof.

Antibodies, also known as immunoglobulins, are protein molecules which usually have specificity for foreign molecules (antigens). Immunoglobulins (Ig) are a class of structurally related proteins consisting of two pairs of polypeptide chains, one pair of light (L) (low molecular weight) chain (κ or λ), and one pair of heavy (H) chains (γ, α, μ, δ and ε), all four linked together by disulphide bonds. Both H and L chains have regions that contribute to the binding of antigen and that are highly variable from one Ig molecule to another. In addition, H and L chains contain regions that are non-variable or constant.

The L chains consist of two domains. The carboxy-terminal domain is essentially identical among L chains of a given type and is referred to as the "constant" (C) region. The amino terminal domain varies from L chain to L chain and contributes to the binding site of the antibody. Because of its variability, it is referred to as the "variable" (V) region.

The H chains of Ig molecules are of several classes, α, μ, σ, α, and γ (of which there are several sub-classes). An assembled Ig molecule consisting of one or more units of two identical H and L chains, derives its name from the H chain that it possesses. Thus, there are five Ig isotypes: IgA, IgM, IgD, IgE and IgG (with four sub-classes based on the differences in the 'constant' regions of the H chains, i.e., IgG1, IgG2, IgG3 and IgG4). Further detail regarding antibody structure and their various functions can be found in, Using Antibodies: A laboratory manual, Cold Spring Harbour Laboratory Press.

In a preferred embodiment of the invention said fragment is a Fab fragment.

In a further preferred embodiment of the invention said antibody is selected from the group consisting of: $F(ab')_2$, Fab, Fv and Fd fragments; and antibodies comprising CDR3 regions.

Preferably said fragments are single chain antibody variable regions (scFV's) or domain antibodies. If a hybidoma exists for a specific monoclonal antibody it is well within the knowledge of the skilled person to isolate scFv's from mRNA extracted from said hybridoma via RT PCR. Alternatively, phage display screening can be undertaken to identify clones expressing scFv's. Domain antibodies are the smallest binding part of an antibody (approximately 13 kDa). Examples of this technology is disclosed in U.S. Pat. Nos. 6,248,516, 6,291,158, 6,127,197 and EP0368684 which are all incorporated by reference in their entirety.

A modified antibody, or variant antibody, and reference antibody, may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and asparatic acid; c) asparagine and glutamine d) arginine and lysine; e) isoleucine, leucine, methionine and valine and f) phenylalanine, tyrosine and tryptophan. Most highly preferred are variants which show enhanced biological activity.

Preferably said antibody is a humanised or chimeric antibody.

A chimeric antibody is produced by recombinant methods to contain the variable region of an antibody with an invariant or constant region of a human antibody.

A humanised antibody is produced by recombinant methods to combine the complementarity determining regions (CDRs) of an antibody with both the constant (C) regions and the framework regions from the variable (V) regions of a human antibody.

Chimeric antibodies are recombinant antibodies in which all of the V-regions of a mouse or rat antibody are combined with human antibody C-regions. Humanised antibodies are recombinant hybrid antibodies which fuse the complimentarity determining regions from a rodent antibody V-region with the framework regions from the human antibody V-regions. The C-regions from the human antibody are also used. The complimentarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not elicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

According to a further aspect of the invention there is provided an isolated nucleic acid molecule wherein said molecule is isolated from a nematode worm which nucleic acid molecule hybridises a nucleic acid sequence as represented by FIG. 1b.

In a preferred embodiment of the invention said nucleic acid molecule hybridises under stringent hybridisation conditions. Preferably said nematode worm is of the genus *Caenorhabditis* spp.

According to a further aspect of the invention there is provided an isolated polypeptide comprising the amino acid as represented in FIG. 1b which polypeptide is modified by addition, deletion or substitution of at least one amino acid residue.

According to a further aspect of the invention there is provided a method of treatment of an animal comprising administering an effective amount of a polypeptide or nucleic acid or vector according to the invention wherein said effective amount induces the apoptotic activity of p53.

In a preferred method of the invention said treatment is of cancer.

According to an aspect of the invention there is provided a peptide comprising an amino acid sequence selected from the group consisting of: GPEETD (SEQ ID NO: 1); DGPEETD (SEQ ID NO: 2); TTLSDG (SEQ ID NO: 3); AEFGDE (SEQ ID NO: 8, amino acids 294-299); or PRNYFG (SEQ ID NO: 4).

In a preferred embodiment of the invention said peptide is at least 6 amino acid residues in length. Preferably the length of said peptide is selected from the group consisting of: at least 7 amino acid residues; 8, 9, 10, 11, 12, 13, 14, 15, 16, 17, 18, 19, or 20 amino acid residues in length. Alternatively the length of said peptide is at least 20 amino acid residues; 30; 40; 50; 60; 70; 80; 90; or 100 amino acid residues in length.

In a further preferred embodiment of the invention said peptide consists of an amino acid sequence consisting of: GPEETD (SEQ ID NO: 1); DGPEETD (SEQ ID NO: 2); TTLSDG (SEQ ID NO: 3); AEFGDE (SEQ ID NO: 8, amino acids 294-299); or PRNYFG (SEQ ID NO: 4).

According to a further aspect of the invention there is provided a pharmaceutical composition comprising at least one peptide according to the invention and at least one anti-cancer agent In a preferred embodiment of the invention said anticancer agent is selected from the group consisting of: cisplatin; carboplatin; cyclosphosphamide; melphalan; carmusline; methotrexate; 5-fluorouracil; cytarabine; mercaptopurine; daunorubicin; doxorubicin; epirubicin; vinblastine; vincristine; dactinomycin; mitomycin C; taxol; L-asparaginase; G-CSF; etoposide; colchicine; derferoxamine mesylate; and camptothecin.

According to a yet further preferred aspect of the invention there is provided a complex comprising a peptide according to the invention and at least one antibody, or active binding part thereof.

In a preferred embodiment of the invention said antibody or fragment is a cell specific antibody. Preferably said cell is a cancer cell.

A complex of a peptide according to the invention and an antibody which specifically binds a cell, preferably a cancer cell, enables the targeting of said peptide to cell. Typically, the complex would be internalised releasing the peptide intracellularly to deliver the peptide to its target. Means to form a complex of antibody and peptide are known in the art and include the use of, for example bi-functional crosslinking agents, these may be hetero-bifunctional or homo-bifunctional. The crosslinkers may be reducible thereby facilitating release of said peptide(s). Cancer specific cell markers are known in the art. For example, tumour rejection antigen precursors. These include by example and not by way of limitation the MAGE, BAGE, GAGE and DAGE families of tumour rejection antigens, see Schulz et al Proc Natl Acad Sci USA, 1991, 88, pp 991-993 which is incorporated by reference.

According to an aspect of the invention there is provided a method of treatment of an animal, preferably a human, wherein said animal would benefit from the induction of apoptosis comprising administering an effective amount of a peptide according to the invention.

According to a further aspect of the invention there is provided a method of treatment of an animal, preferably a human, wherein said animal would benefit from the induction of apoptosis comprising administering an effective amount of a composition according to the invention In a preferred method of the invention said treatment is cancer treatment.

An embodiment of the invention will now be described by example only and with reference to the following figures:

Figure 1a is the nucleic acid sequence of human iASPP (SEQ ID NO: 6); Figure 1b is the *C. elegans* nucleic acid sequence of iASPP (SEQ ID NO: 7);

FIG. 2a is the amino acid sequence of human iASPP (SEQ ID NO: 8); FIG. 2b is the *C. elegans* amino acid sequence of iASPP (SEQ ID NO: 9);

FIG. 6 illustrates various experiments showing the interaction of *C. elegans* iASPP and p53;

FIG. 7 illustrates a homology comparison between *C. elegans* iASPP and human iASPP.

FIG. 9 illustrates the effect of RNAi on *C. elegans* iASPP expression;

Figure 11:
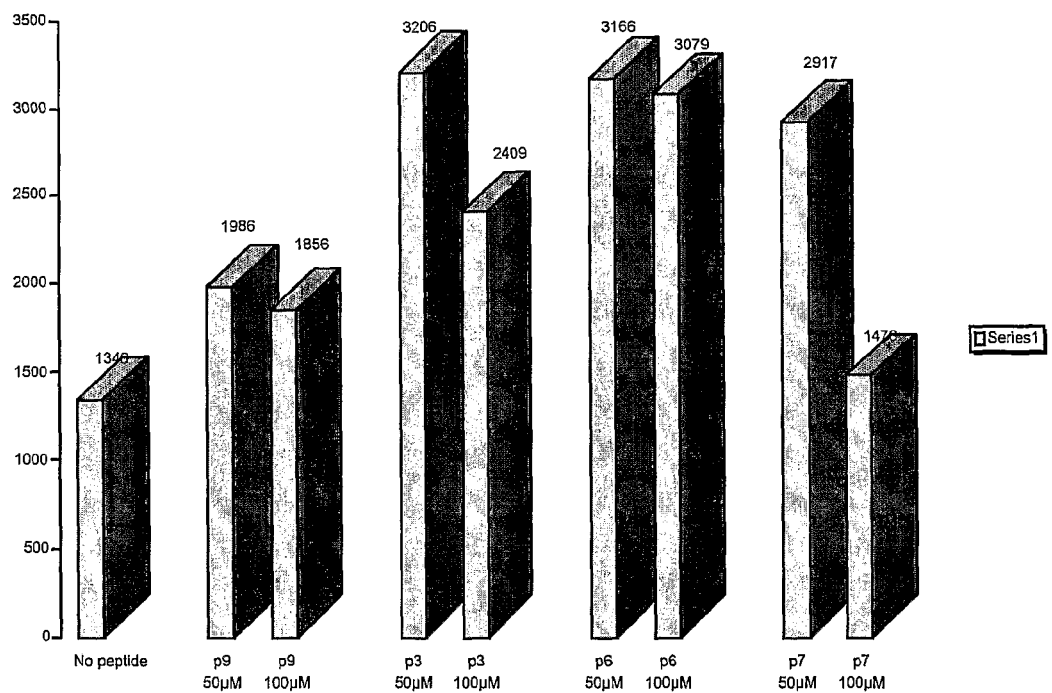
Figure 12:
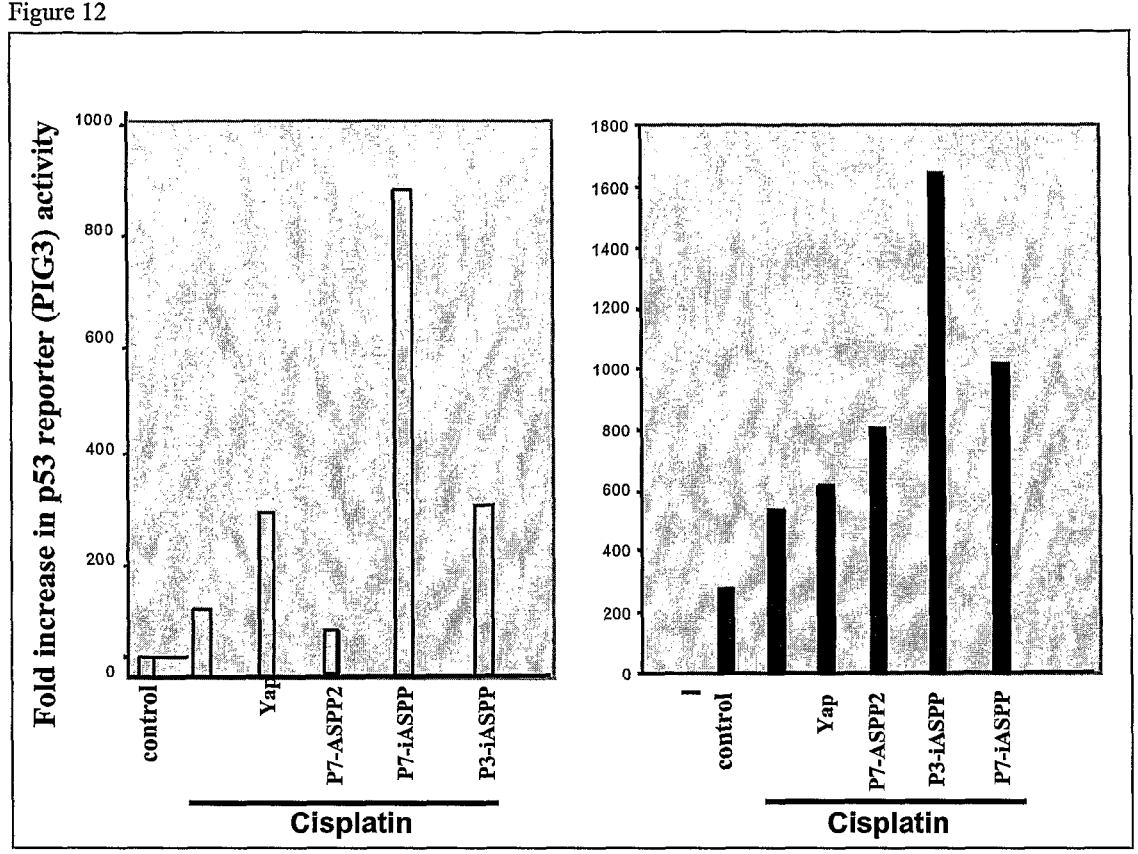
Figure 14A:
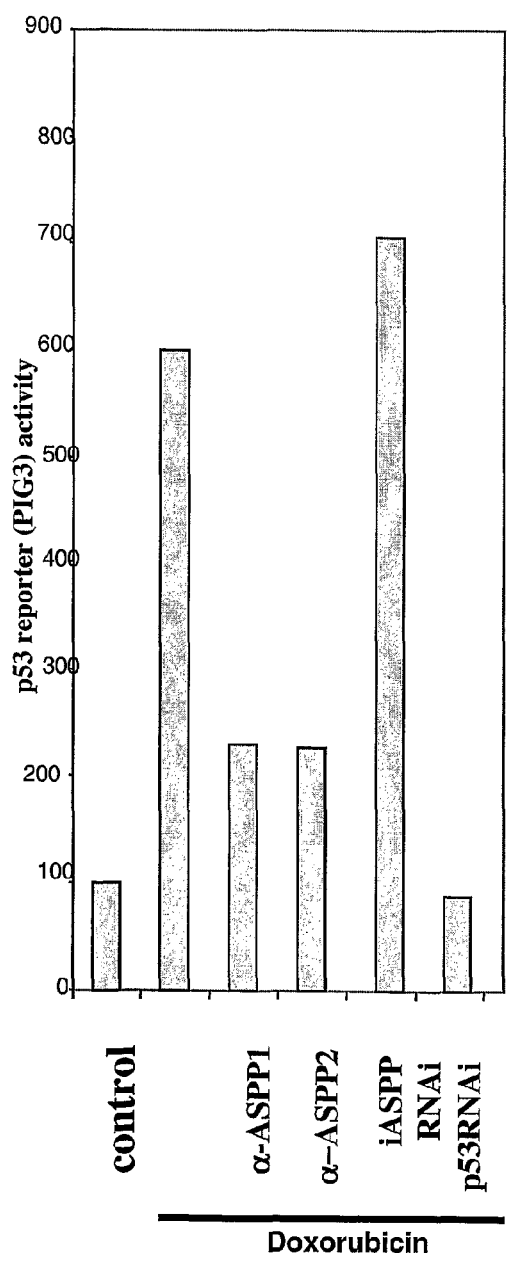
Figure 14B:
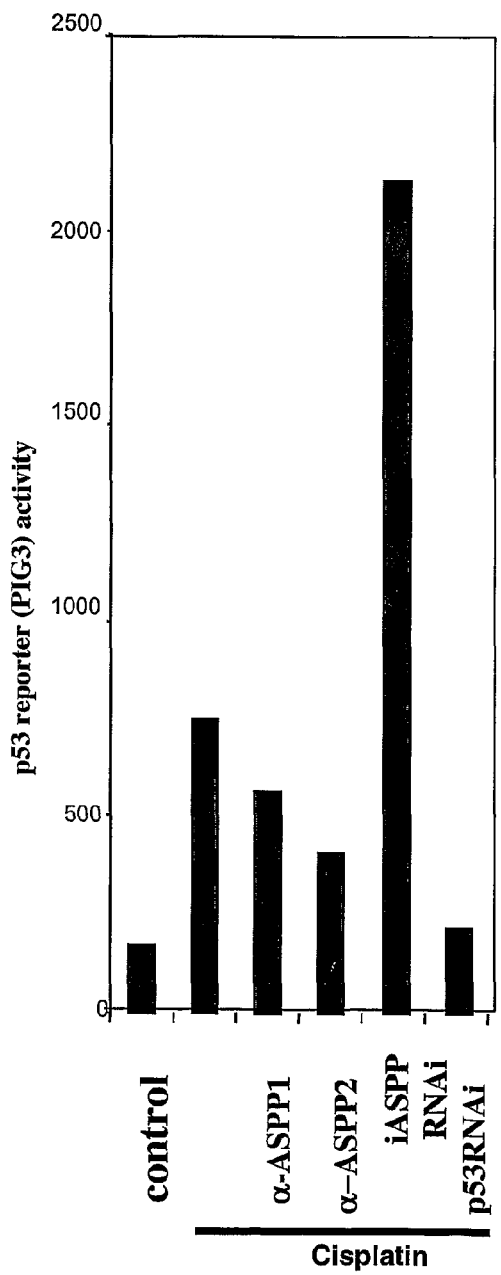
Figure 15:
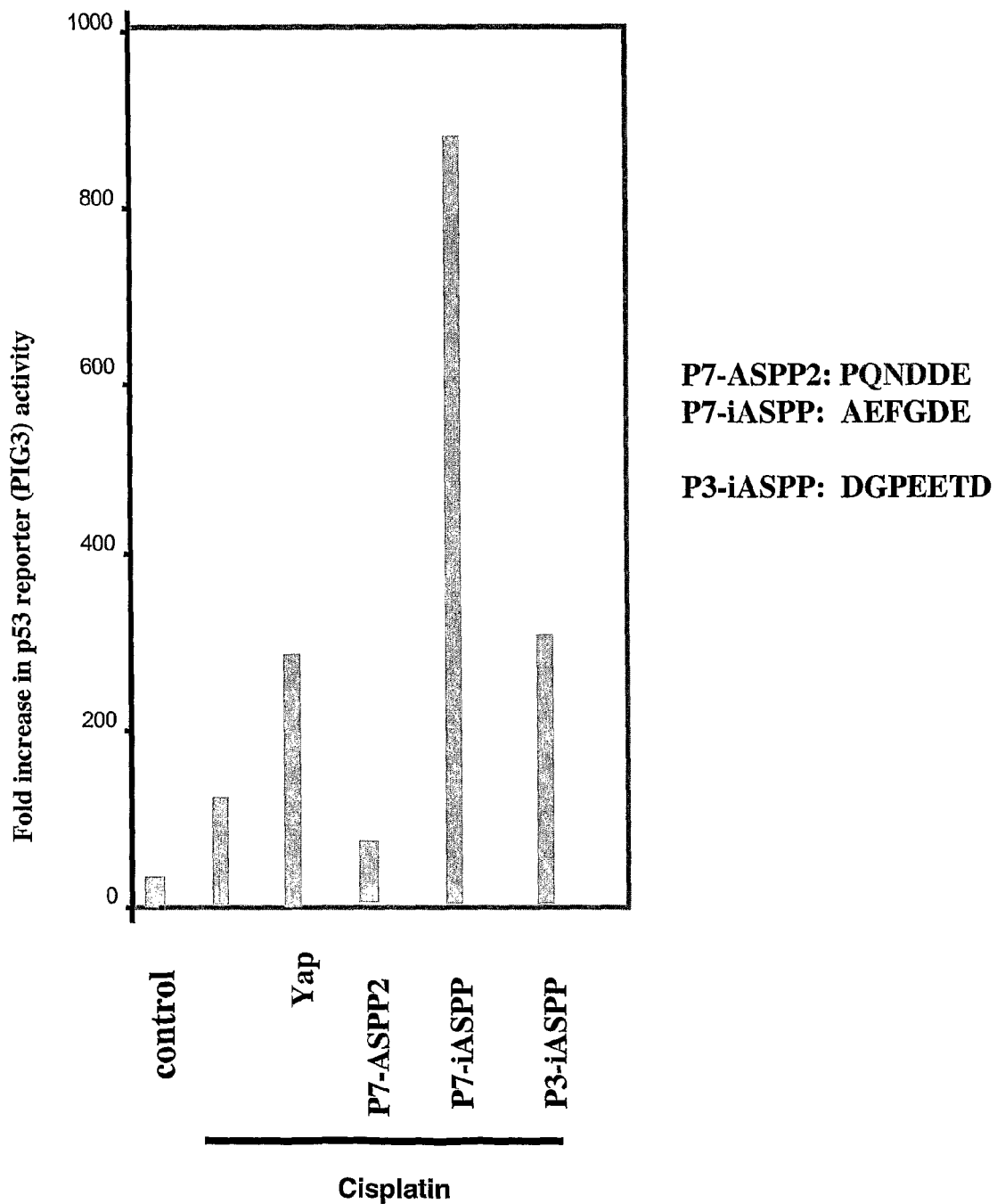

FIG. 11 Influence of peptides on transactivation level of Bax-Luc reporter. Cells were transfected with Bax reporter gene and exposed to UV (20J/m2). Peptides were added for 24 hours in medium at two different concentrations as indicated;

FIG. 12 illustrates the influence of peptides on Pig3 reporter activity for 12 hours. Transactivated cells were grown with medium containing Arg-tagged peptides at two concentrations. The left bar graph represents the transactivation activity at a concentration of 25 uM and the second is with a concentration of 50 uM. Yap peptide is used as a control peptide here instead of p9. Except for the control, cells were treated with cisplatin (3 ug/ml);

FIG. 13 illustrates the effects of various chemotherapeutic drugs on p53 induced apoptosis;

FIG. 14a illustrates the effects of antisense or si-RNA of ASPP1, ASPP2 or iASPP, in combination with the activity of the anti-cancer agent doxorubicin; FIG. 14b illustrates the effects of antisense or si-RNA of ASPP1, ASPP2 or iASPP in combination with the activity of the anti-cancer agent cisplatin;

FIG. 15 illustrates the activity of inhibitory peptides in combination with cisplatin on ASPP1, ASPP2 and iASPP.

Materials and Methods

Cell Culture, Antibodies and Plasmids

Saos-2, MCF-7, and U2OS cells were grown in DMEM supplemented with 10% FCS, 100 IU/ml penicillin-streptomycin and 2 mM glutamine. Anti-p53 antibodies DO-1and DO-13 are monoclonal antibodies while CM-1 is a rabbit polyclonal antibody specific to p53. The V5 and 9E10 epitopes are recognised by the mouse monoclonal antibodies V5and 9E10 respectively. The mouse monoclonal PC-10 is specific to the PCNA protein. CD20Leu is an FITC conjugated monoclonal antibody specific for the cell surface marker CD20 (Becton Dickinson). The mouse and rabbit antibodies to ASPP1 and ASPP2 were described previously[1]. Mouse and rabbit antibody to iASPP (peptide RLQPALPPEAQSVPELEE (SEQ ID NO: 5) was produced as described by Harlow and Lane [13]. All expression plasmids used in this study were driven by the CMV immediate early promoter. ASPP1, iASPP and Ce-iASPP are tagged with V5 epitope while Ce-p53 is tagged with 9E10 epitope.

DNA Transfection

The transfection mix included the DNA of interest in 1×HBS buffer (280 mM NaCl, 10 mM KCl, 1.4 mM $Na_2HPO_4.2H_2O$, 12 mM Glucose, 39 mM HEPES, adjusted to pH 6.9-7.3) precipitated with 2.5 M $CaCl_2$. The transfection mix was added dropwise to the cells and washed off after 6 hours with DMEM. 16-24 hours following the wash, cells were lysed either in Reporter lysis buffer (Promega) for Luciferase assays and western blots or in NP40 lysis buffer for western or immunoprecipitation procedures.

Transactivation Assays

For transcriptional assay, $5 \times 10^5$ Saos-2 cells were plated 24 hr prior to transfection in 6 cm dishes. Various combinations of plasmid DNA were transfected using the following amounts. All transfection assays contain 1 μg of reporter plasmid. 50 ng of wild type human p53, 100 ng of plasmid expressing C. elegans p53, 4 μg of ASPP2, or 8 μg of ASPP1, 5 μg of human iASPP or 7.5 μg of Ce-iASPP were used as indicated. After transfection, the cells were lysed in Reporter Lysis Buffer (Promega, Wis., USA) 16-24 hr post-wash and assayed using the Luciferase Assay kit (Promega, Wis., USA). The fold activation of a particular reporter was determined by the activity of the transfected plasmid above the activity of vector alone. The fold increase of p53 transactivation activity by ASPP was obtained by the activity p53 in combination with ASPP divided by the activity of p53 alone on the promoters used in each assay.

Cell Transformation Assay

Rat Embryo Fibroblasts (REFs) obtained from Biowhittaker were grown in DMEM to 50% confluence in a 90 mm dish. Cells were then transformed as described previously[14]. Briefly, 2 μg of EJ ras 6.6, 2 μg of pCE (E1A), 5 μg of pCB6-16E, 5 μg of wild type human p53, 1 μg or 5 μg of human or C. elegans iASPP were transfected into the REFS as indicated. All the cells were transfected with the same amount of plasmid DNA expressing neo gene. The transfected cells were then selected with 400 μg/ml of G418 and the morphologically transformed colonies were scored after 3-4 weeks after transfection.

Flow Cytometry

For FACS analysis, $10^6$ Saos-2 cells were plated 24-48 h prior to transfection in 10 cm plates. The cells were then transfected with 2 μg of a plasmid expressing CD20. CD20 expression was used as a transfection marker. The transfections consisted of 1 μg of human p53 or 4 μg of Ce-p53, 10 μg of ASPP1 and ASPP2, 2 μg of Bax, 15 μg of anti-sense iASPP, 7.5 μg-10 μg of human iASPP or 7.5 μg of Ce-iASPP plasmid as indicated. 36 hours after the transfection, both attached and floating cells were harvested using 4 mM EDTA/PBS and stained with FITC conjugated anti-CD20 antibody CD20Leu. For each experiment, one dish of cells was transfected with the control vector only without CD20. These cells were later stained with antibody CD20Leu under the same conditions as those co-transfected with CD20 plasmid to serve as a negative control. The cells lacking expression of CD20 plasmid were used to set the base line to allow the gating of the CD20 positive (and hence transfected) cells. After staining with the antibody CD20Leu, the cells were fixed and stained with propidium iodide. The DNA content of all the cells expressing CD20 was analysed using the flow cytometer (Becton Dickson) as described[15].

Protein Biochemistry

For western blotting, cells grown in monolayers were washed with 1×PBS and lysed in either NP40 lysis buffer (1% Nonidet P40, 50 mM Tris pH8.0, 150 mM NaCl, 1 mM EDTA pH 8.0) or luciferase reporter lysis buffer. The protein concentration of the cell extracts was determined against a standard curve using the BioRad protein assay system (BioRad). Between 15-100 μg of extract was mixed with 5× sample buffer and loaded on SDS-PAGE gels. The gels were wet transferred on to Protran nitrocellulose membrane and the resulting blots blocked in 10% reconstituted milk powder in 1×PBS. Subsequently the blots were incubated with primary antibody prepared either in tissue culture medium or as undiluted hybridoma supernatant and incubated with the appropriate secondary HRP conjugated antibody (Dako). In between each stage the blot was washed with repeat changes of TBST (10 mM Tris pH 8.0, 150 mM NaCl, 0.5% Tween 20). The blot was exposed to hyperfilm following the use of ECL substrate solution (Amersham Life Science).

For immunoprecipitation cells were lysed in NP40 lysis buffer on ice for 30 minutes and pre-cleared with protein G beads for 1 hour at 4 C. The protein concentration was determined and 1000 μg of the extract was incubated with antibody pre-bound to protein G beads for 4 hours at 4 C. The beads were washed twice in NP40 lysis buffer and twice in NET buffer (50 mM Tris pH 8.0, 150 mM NaCl, 1 mM EDTA pH 8.0). The IP beads were mixed with 5× sample buffer and loaded onto a SDS-PAGE gel.

In vitro Translation and in vitro Immunoprecipitation

ASPP family members and p53 were in vitro translated and labelled with $^{35}$S-Methionine using the TNT T7 Quick coupled Transcription/Translation System (Promega). For the experiments shown in FIG. 1E, 15, 30 and 45 μl of in vitro translated lysates of iASPP were added in addition to p53 and ASPP2. Rabbit anti-p53 antibody CM1 was used to detect the presence of unlabelled p53.

For FIG. 6A, 5-10 μl of human iASPP lysate (unlabelled) was incubated with 15 μl of the lysate containing the in vitro translated Ce-p53. The mixture of proteins was allowed to co-translate at 30 C for 1 hr. 200 μl of phosphate-buffered saline (PBS) was then added to the mixture of proteins and incubated at 4 C for a further hour on a rotating wheel. The anti-V5 antibody immobilised on protein G agarose beads was added to the binding reactions and incubated on a rotating wheel at 4 C for 16 hours. The beads were then washed with PBS. The bound proteins were released in SDS gel sample buffer and analysed by 10% SDS-polyacrylamide gel electrophoresis (PAGE). Ce-p53 was detected by autoradiography and Human iASPP was detected by anti-V5 antibody following a western blot. For the rest of the figures, the proteins were labelled with $^{35}$S -Methionine and immunoprecipitated as above using the indicated antibodies. Results were visualised using autoradiography.

In vivo Labelling of Cells with 35S -methionine and $^{35}$S-cysteine

U20S cells in the absence or presence of transfected plasmids (as indicated in FIGS. 1A and 2C) were washed with PBS and then incubated with 250 µci/ml of $^{35}$S-methionine and 250 µci of 35-cysteine in DMEM lacking both methionine and cysteine for 2 hours at 37 C. Cells were then washed with PBS before harvesting. For FIG. 2C, twenty four hours after transfection the cells were in vivo labelled with $^{35}$S-methionine and $^{35}$S-cysteine for 2 hrs. Cells expressing CD20 (transfected cells) were stained with FITC-conjugated anti-CD20 antibody. A biotin conjugated anti-FITC antibody was then added to the cell pellet, and after the incubation, the cells were mixed with streptavidin conjugated magnetic beads to isolate the CD20 expressing cells. The cells were then lysed with NP40 lysis buffer and the proteins immunoprecipitated with mouse anti iASPP antibody. The immunoprecipitates were washed with NET buffer and resolved by SDS-PAGE and autoradiography.

Cell Fixation

Monolayers of cells were grown in 30 mm dishes and washed with 1×PBS. Cells were fixed with 1 ml of 4% paraformaldehyde for 15 minutes and then washed in 1×PBS. 1 ml of 0.2% Triton-X100 in 1×PBS was used to permeabilise the cells for 2 minutes and this was washed off with three washes of 1×PBS. Primary antibody was prepared in tissue culture medium at the appropriate concentration and added to the dishes for 3 hours. The dishes were washed with 1×PBS and the secondary antibody of either anti-rabbit TRITC (Tetramethyl rhodamine isothiocyanate) or anti-mouse FITC (Fluorescein isothiocyanate) prepared in tissue culture medium at the manufacturers recommended dilution (Sigma, UK) and added to the dishes for one hour. The cells were washed in 1×PBS and left to air dry. Citifluor shielding agent (Citifluor, UK) was applied as a drop to the surface of the cells and a cover slip placed on top. A drop of immersion oil on top of the cover slip allowed the immunocomplexes to be visualised using a Zeiss Axiophot fluorescence microscope. Antibodies 9E10 and V5 were used to detect the expression of epitope tagged Ce-p53 (9E10), human iASPP (V5) and Ce-iASPP (V5) respectively. Human p53 was detected by DO.1 antibody.

Cloning Ce-p53 and Ce-iASPP cDNA cDNAs carrying the complete coding regions of Ce-ape-1 (iASPP) and Ce-cep-1 (p53) were generated by RT-PCR using the Promega Access kit, cloned into the vector pCR4-TOPO (Invitrogen) and sequenced. C. elegans p53 and iASPP were then subcloned into a mammalian expression vector pcDNA3 in frame with the epitope of 9E10 and V5 respectively. The full-length Ce-ape-1 is predicted to be trans-spliced to SL1 (Y. Kohara, unpublished).

RNA Interference (RNAi) and Cell Corpse Assays

RNAi was performed by feeding or microinjection using established procedures (Fire et al., 1998; Timmons and Fire, 1998) In order to eliminate Ce-iASPP and Ce-p53 activity by RNAi, N2 animals were first subjected to Ce-iASPP RNAi feeding. Subsequently, 20 F1 animals were removed from the feeding plate, injected with Ce-p53 dsRNA and returned to independent Ce-iASPP dsRNA feeding plates. The F2 progeny of animals fed Ce-iASPP (+/−injection of Ce-p53 dsRNA) were stained with SYTO12 and apoptotic corpses scored as described12. Hence, because all animals have been subjected to Ce-iASSP feeding RNAi, any differences in the mean number of apoptotic cell corpses detected in the two populations are likely to result from Ce-p53 dsRNA injection.

EXAMPLES iASPP is the Most Conserved Member of the ASPP Family

Figure 3A:
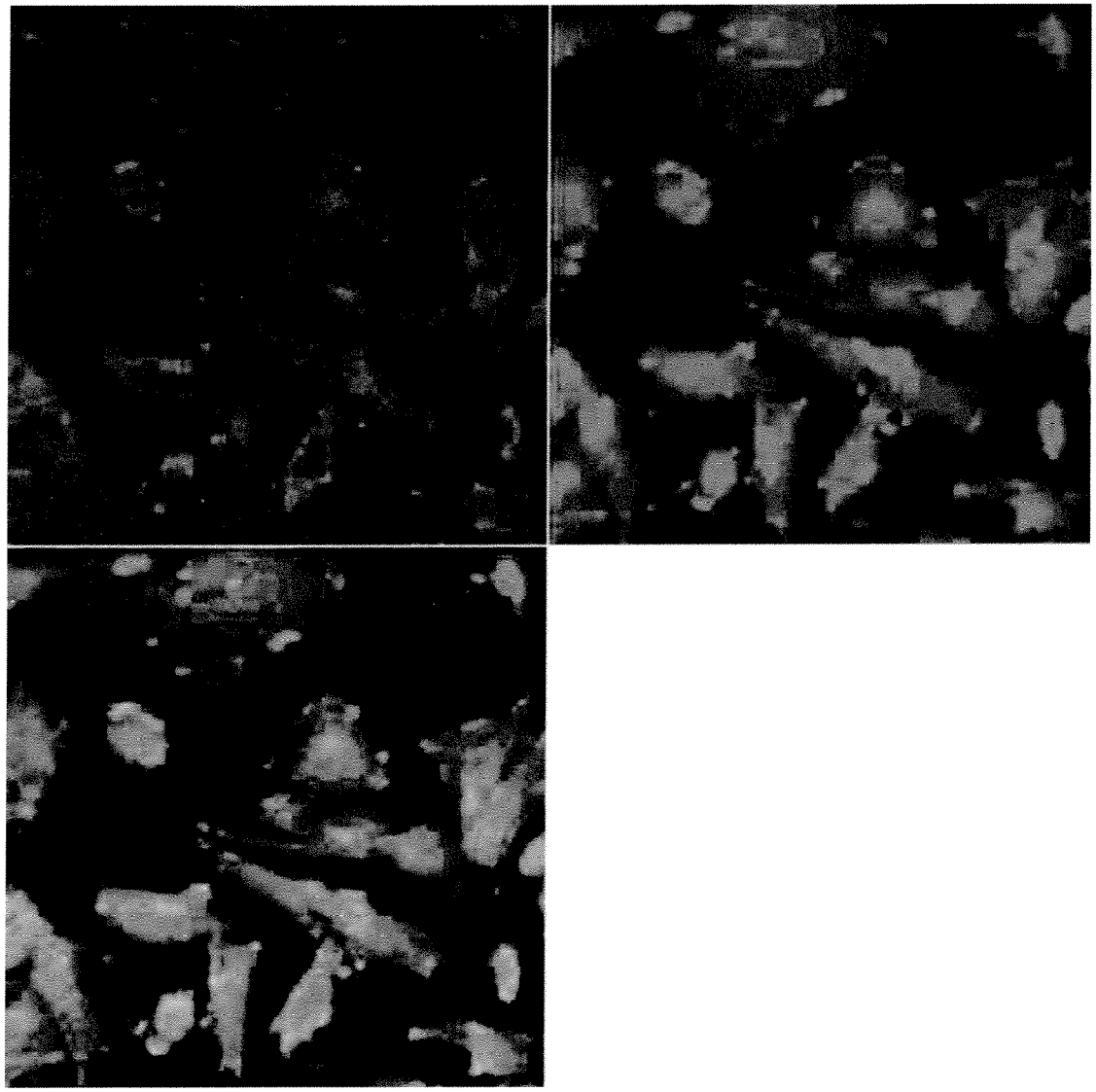
FIG. 3 illustrates that FITC labelled peptide (3a) DGPEETD (SEQ ID NO: 2) and (3b) TTLSDG (SEQ ID NO: 3) can penetrate cells.
Figure 3B:
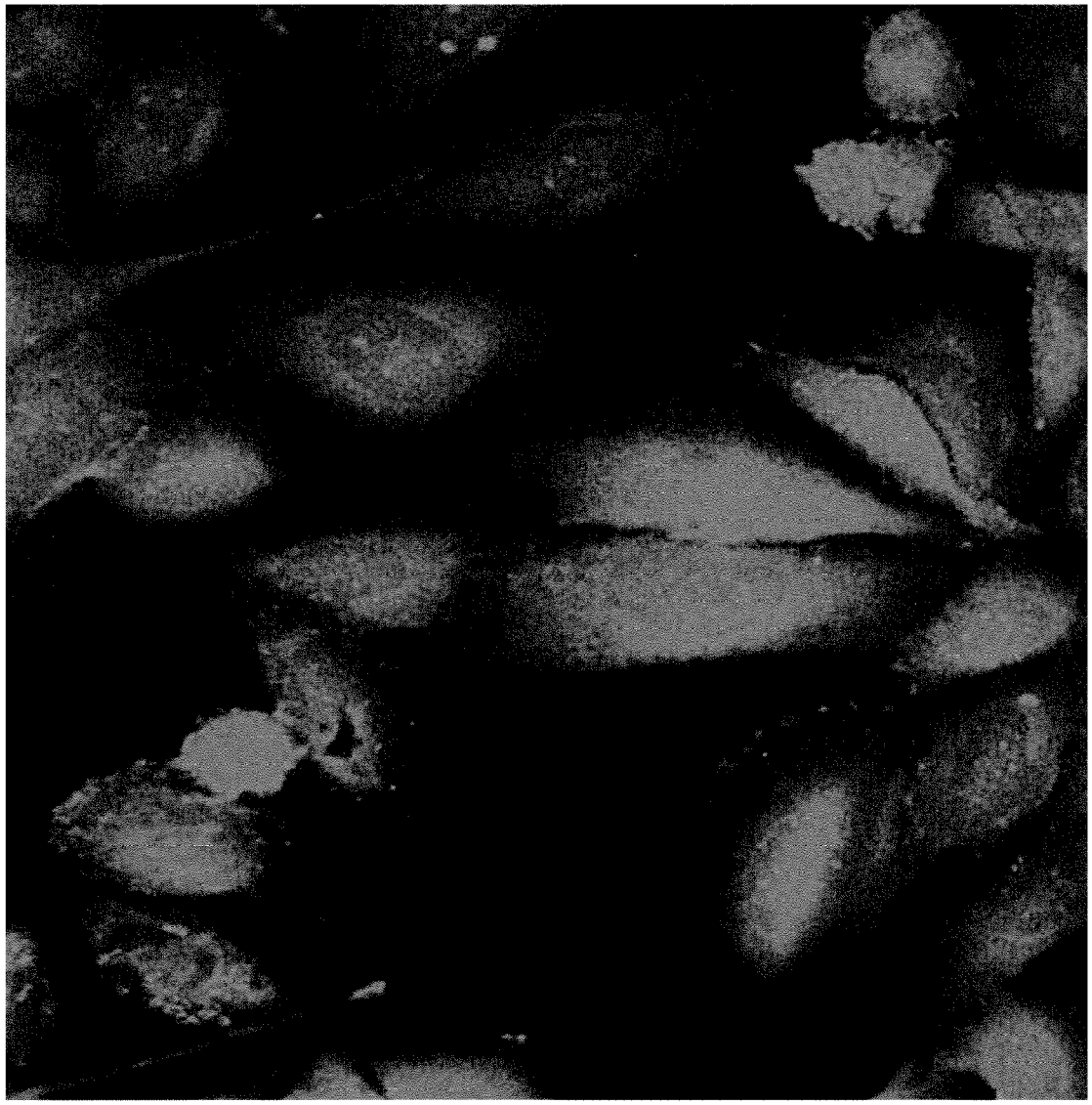
Figure 4:
FIG. 4 illustrates the stimulation of the Bax promoter by p53 after incubation with various peptides, in particular DGPEETD (SEQ ID NO: 2)
Figure 5:
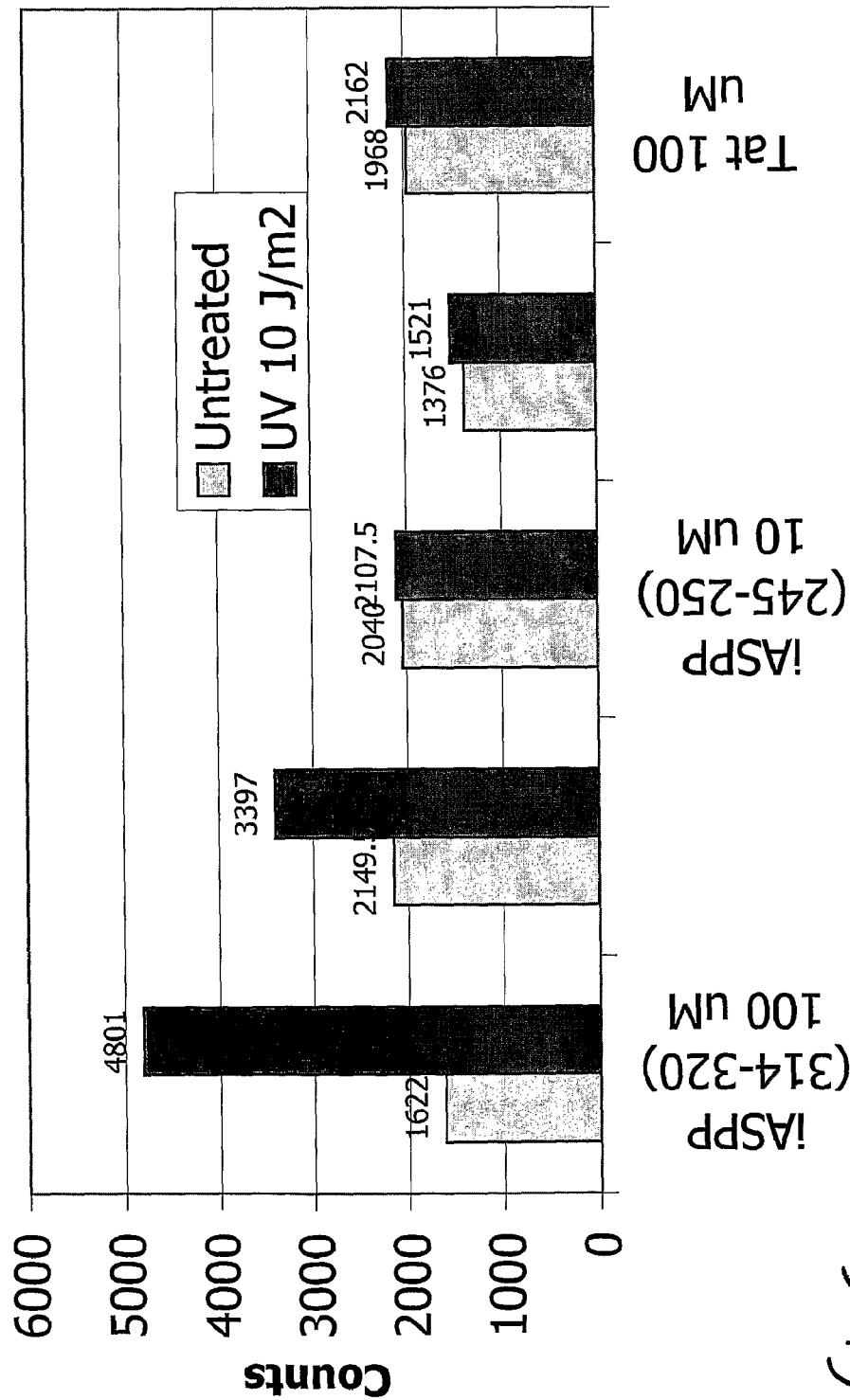
FIG. 5 illustrates the stimulation of p53 transactivation in a human tumour cell line U2SO after UV damage of DNA in the presence of peptide DGPEETD (SEQ ID NO: 2)
Figure 8B:
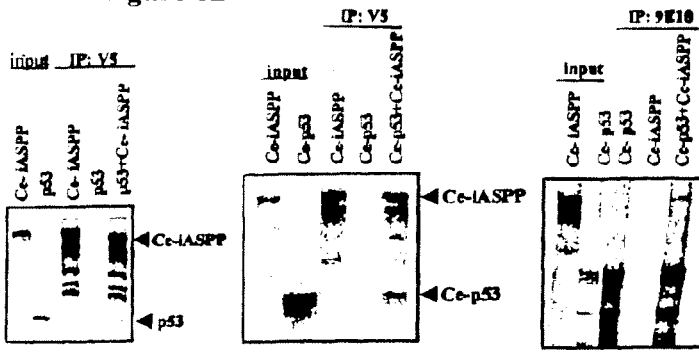
FIG. 8 illustrates further experiments showing the interaction of *C. elegans* iASPP and p53.

Sequence analysis indicates that the C. elegans p53 gene, cep-1, is a distant member of the p53 family; however, the residues critical for ASPP and DNA binding activity appear to be conserved[3,4] Hence, we searched the C. elegans genome for an ASPP homologue and found that F46F3.4 is the only C. elegans gene encoding a protein with significant sequence homology to all three members of the ASPP family. The gene corresponding to F46F3.4 has been named ape-1 (for apoptotic enhancer) based on the mutant phenotype produced by ape-1(RNAi) (see below); however, the protein product will henceforth be referred to as Ce-iASPP. Ce-iASPP consists of 769 amino acids; sequence comparisons reveal that the C-terminus of Ce-iASPP is the region most conserved with other ASPP members (FIG. 7). It was previously shown that the C-terminus of ASPP2 interacts with p53. Moreover, all but one (6 out of 7) residue involved in this interaction are conserved in both iASPP and Ce-iASPP. Taken together these results suggested that Ce-iASPP might interact with both human and C. elegans p53. This was tested in vitro by co-immunoprecipitation. As shown in FIG. 8B, Ce-iASPP interacts with both human and Ce-p53. The interaction between Ce-p53 and Ce-iASPP was further confirmed by reciprocal immunoprecipitation (FIG. 8B, right panel).

Figure 8C:
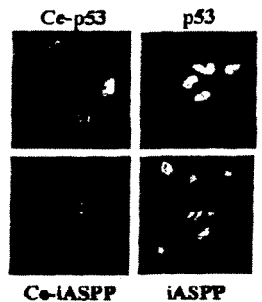
Figure 8D:
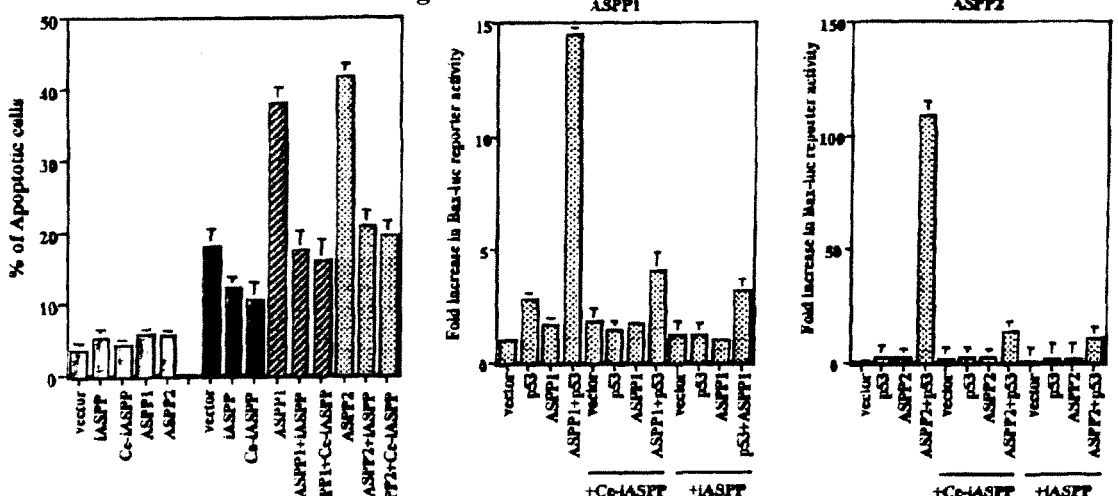
Figure 8E:
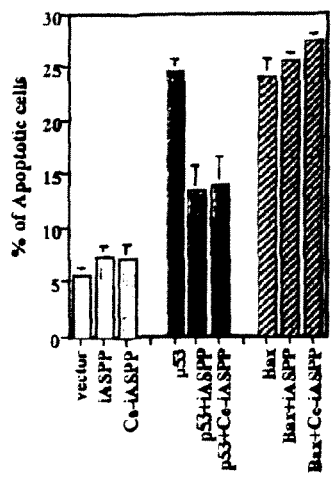
Figure 8F:
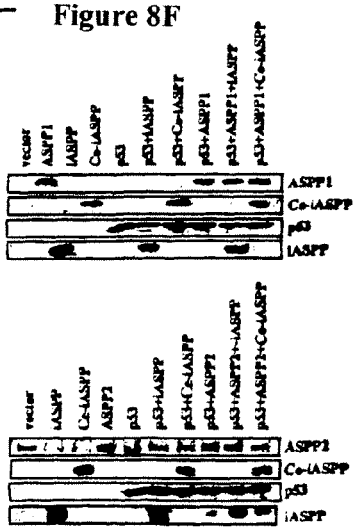
Figure 8G:
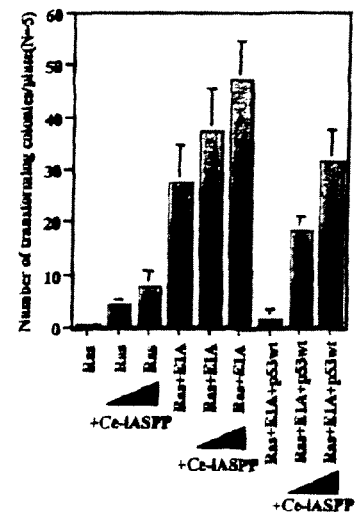

Ce-iASPP contains the hallmark ankyrin repeats and SH3 domain found in other ASPP family members and is expressed in the cytoplasm and nucleus of human cells (FIG. 8C). The expression of human iASPP is predominantly nuclear but cytoplasmic staining is also detectable. Both human and C. elegans p53 are primarily expressed in the nucleus of transfected human cells (FIG. 8C). Since ASPP and iASPP can positively and negatively regulate the apoptotic function of p53, respectively, we tested the effect of Ce-iASPP on the activities of p53. When Ce-iASPP was co-expressed with human p53 in mammalian cells, it produced a small reduction in the transactivation and apoptotic function of p53, presumably by inhibiting endogenous ASPP function. However, in the presence of ASPP1 or ASPP2, co-expression of Ce-iASPP prevented ASPP1 or ASPP2 from stimulating the transactivation and apoptotic function of p53 to the same extent as human iASPP (FIG. 8D). Furthermore, the ability of human and C. elegans iASPP to inhibit apoptosis is p53-dependent since they both failed to inhibit Bax induced apoptosis under the same conditions (FIG. 8E). The ability of iASPP to inhibit the activity of p53 is not due to the reduced expression of p53 (FIG. 8F). Like human iASPP, the Ce-iASPP also has oncogenic activity. The expression of Ce-iASPP enhanced the transforming activity of ras and E1A. Moreover, expression of Ce-iASPP inhibited the suppressor function of wild type human p53 (FIG. 8G). These results demonstrate that Ce-iASPP is more likely to be an orthologue of human iASPP than of ASPP. Also, the ability of Ce-iASPP to inhibit p53 suggests that the regulation of p53 apoptotic function by the ASPP family of proteins is evolutionarily conserved.

The Regulation of p53 by ASPP Family of Proteins is Evolutionarily Conserved It was unclear whether Ce-p53 could induce apoptosis in mammalian cells because of the limited sequence similarity between human and *C. elegans* p53, although most of the Ce-p53 residues that contact ASPP are conserved. If Ce-iASPP inhibits the activities of human p53 in a manner similar to that of human iASPP, this argues that the regulation of p53 by the ASPP family has been evolutionarily conserved. This further suggests that the activities of Ce-p53 could be subject to regulation by the ASPP family of proteins. To address these issues, Ce-p53 was tested for its ability to interact in vitro with members of the human ASPP family by co-immunoprecipitation. As shown in FIG. 6A, Ce-p53 interacts with ASPP2 and iASPP. The expression of Ce-p53 induced apoptosis in human cells with an efficiency similar to human p53. Remarkably, expression of human ASPP, ASPP2 in particular, significantly enhanced the ability of Ce-p53 to induce apoptosis to an extent similar to human p53 and the expression of human iASPP also inhibited the apoptotic function of Ce-p53 (FIG. 6B). In addition, both human and *C. elegans* iASPP inhibited Ce-p53 induced apoptosis to the same extent (FIG. 6C). The ability of Ce-p53 to transactivate p53 target gene promoters, such as Bax-luc, was also tested and was found to be much lower than that of human p53. Interestingly, co-expression of ASPP2 and Ce-p53 resulted in a very small but detectable increase in the transactivation function of Ce-p53, indicating that the human ASPP family could regulate Ce-p53 in a manner similar to that of human p53 (FIG. 6D). The small increase in the transactivation function of Ce-p53 by ASPP2 is not observed on the mdm2 promoter. All of these results suggest that the residues conserved between human and *C. elegans* p53 are crucial and sufficient for the apoptotic function of p53 and for p53 to be regulated by the ASPP family.

iASPP is an Evolutionarily Conserved Inhibitor of p53 in vivo

Like human p53, one of the most important functions of *C. elegans* p53 is its ability to induce apoptosis in germ cells in response to DNA damage[3,4]. Knowing that co-expression of human or *C. elegans* iASPP can inhibit the apoptotic function of p53 in mammalian cell lines, we hypothesised that expression of Ce-iASPP might similarly protect *C. elegans* germ cells from death by apoptosis. This question was addressed in vivo using RNA mediated interference (RNAi)[5]. Depletion of endogenous Ce-iASPP increased the number of germ cells undergoing apoptosis, indicating that the normal function of Ce-iASPP is to inhibit apoptosis (FIG. 9A, lanes 1 and 5, 6). The enhancement of germ cell apoptosis caused by depletion of Ce-iASPP was not detected when RNAi was performed in a mutant lacking the *C. elegans* CED-3 caspase, indicating that the core apoptotic machinery is involved in this process (FIG. 9A, lanes 3 and 4)[6]. We also obtained additional support for the hypothesis that the primary role of Ce-iASPP is to inhibit the pro-apoptotic activity of Ce-p53, which is normally stimulated in response to genotoxic stress[3,4]. First, it was found that the increase in the number of *C. elegans* germ cells undergoing apoptosis after depletion of Ce-iASPP was abrogated by simultaneously depleting Ce-p53 by RNAi (FIG. 9A, compare lanes 5, 6 and 8). Moreover, the depletion of both Ce-iASPP and Ce-p53 by RNAi did not completely eliminate apoptosis, but instead returned the number of germ cells undergoing apoptosis to wild-type physiological levels. Second, the increase in the number of apoptotic germ cell corpses detected after wild type worms were exposed to 100-Gy IR was no greater than that observed after depletion of Ce-iASSP by RNAi in the presence or absence of exposure to 100-Gy IR (FIG. 9A, lanes 2 and 7). These results clearly demonstrate that iASPP is an important inhibitor of p53 function in *C. elegans*, although we can not exclude the possibility that a genetic knockout might reveal that Ce-iASPP has additional activities. Since the regulation of p53 by the ASPP family is highly conserved, it is likely that iASPP is also a key inhibitor of p53 in other organisms including humans.

We show here that iASPP is the most phylogenetically conserved inhibitor of p53, so far identified, and also the most evolutionarily conserved member of the ASPP family. Remarkably, the ability of ASPP family members to regulate the apoptotic function of p53 has been conserved between *C. elegans* and human. This argues that the apoptotic function of p53 is likely to be more conserved than its ability to induce cell cycle arrest; this agrees with recent observations showing that ectopic expression of both *C. elegans* and *Drosophila* p53 induces apoptosis but not cell cycle arrest[3,4,7,8]. In *C. elegans* p53-mediated apoptosis appears to play an important role in maintaining the fidelity of germ cells, which might have incurred DNA damage[3,4]. Interestingly, the most important tumour suppressor function of p53 is also linked to its ability to induce apoptosis. Therefore, ASPP family members, the evolutionarily conserved regulators of p53, must play a critical role in tumourigenesis.

The Oncoprotein iASPP iASPP shares more sequence similarity with the N-terminally truncated ASPP2 mutant 53BP2 than the full-length ASPP. Expression of iASPP inhibited the apoptotic function of p53. Like 53BP2, the most profound effect of iASPP on the apoptotic function of p53 is mediated through its ability to act as a competitor of ASPP. However, in *C. elegans*, iASPP is the only gene that has homology to the human ASPP family. Thus iASPP directly inhibits the apoptotic function of p53 in *C. elegans*. A similar mechanism might also apply in mammalian cells. In agreement with this, iASPP antisense RNA induced a 3 to 5-fold increase in apoptotic cells in U2OS and MCF7 cells. In this latter model, ASPP could stimulate the apoptotic function of p53 by removing the negative effects that iASPP imposed on p53. The failure of iASPP antisense RNA to produce a significant increase of apoptosis in cisplatin treated U2OS and MCF7 cells might be due to the fact that cisplatin stimulates the apoptotic function of p53 by increasing the activities of ASPP. This, in turn, might explain why the expression of ASPP antisense RNA generated a profound inhibitory effect on apoptosis induced by cisplatin. It is also under this condition that the anti-apoptotic function of iASPP is most pronounced. Thus the apoptotic function of p53 is negatively regulated by iASPP and positively regulated by ASPP. The competition between these two opposing signals could determine the apoptotic state of p53 and ultimately cell fate. Regardless of whether iASPP acts as a dominant negative regulator of ASPP or a direct inhibitor of p53, a competition between iASPP and ASPP for binding to p53 is critical for the apoptotic function of p53. Consistent with this model, a change in the percentage of p53 complexed with ASPP2 was seen in response to DNA damage. It is likely that the percentage of p53 complexed with iASPP and ASPP would be regulated by signals that induce death or survival.

Being an inhibitor of p53, iASPP enhanced the transforming activities of oncogenes such as ras plus E7 or E1A of human papilloma virus and adenovirus but not ras plus mutant p53. This is particularly interesting since E7 and E1A are known to induce p53-dependent apoptosis[9]. While E7 and E1A can bind and inactivate the tumour suppressor function of Rb, their oncogenic function is largely reduced due to their ability to activate p53-dependent apoptosis. Proteins that can inhibit apoptosis induced by E7 and E1A would enhance the oncogenic function of E7 and E1A. Therefore, like the dominant negative p53 mutants, iASPP was able to stimulate the oncogenic function of E7 and E1A by inhibiting the apoptotic function of p53. It is important to point out that iASPP was not as active as mutant p53, p53H175 or p53L173 in co-operating with ras to transform REFs under the experimental conditions described here. Part of the reason was due to the low expression level of iASPP in the assay (data not shown). However, the differences in the transforming activities of iASPP and mutant p53 might also be caused by other known activities of mutant p53, which are independent of its ability to act as a simple dominant negative inhibitor of p53. Nevertheless the ability to confer cellular resistance to the cytotoxic effects of UV and cisplatin suggested that the overexpression of iASPP would be selected for in human tumours expressing wild type p53. Consistent with this, iASPP expression is increased in human breast carcinomas expressing wild type p53. The majority of tumours (7 out of 8) expressing high levels of iASPP also express wild type p53 and normal levels of ASPP, indicating that iASPP is an inhibitor of ASPP in vivo. Our previous study showed that the expression levels of ASPP1 and ASPP2 were down regulated in 60% of human breast tumours express wild type p53. Taken together, the abnormal expression of ASPP family members would account for almost 80% of human breast carcinomas examined. The ASPP family members are encoded by three different genes located on different chromosomes (data not shown). We do not know why the frequency of human breast carcinomas showing down regulation of ASPP is much higher than those showing increased expression of iASPP. However, it is possible that the expression pattern of the ASPP family members varies in different types of human tumours. The percentage of tumours with altered ASPP expression could also differ in various tumour types. Nevertheless, inhibiting the oncogenic function of iASPP could provide an important new strategy to treat tumours expressing wild type p53.

Evolutionarily Conserved Regulation of p53 by the ASPP Family

Sequence comparison reveals that there is 38% identity between the human and *C. elegans* iASPP amino acid sequences; within the ankyrin repeats and SH3 domain, the homology is as high as 78% (residues 154-227 of human iASPP and 557-630 of Ce-iASPP, 55/74 residues are similar). Most of the iASPP residues contacting p53 are conserved. The structural conservation between human and *C. elegans* iASPP is reflected by their ability to regulate p53 function in human cells. Like human iASPP, *C. elegans* iASPP interacts with and inhibits the transactivation and apoptotic function of human p53 in cell lines. The conservation of ASPP/p53 regulation is further demonstrated in a study of *C. elegans* p53 in human cells. It is interesting and important to point out that the sequence homology between human and *C. elegans* p53 is very limited (13.7% identity at protein level). The highest level of p53 homology between the two species is around 50% in a very limited region (residues 9/18 residues are similar). However, many of the ASPP2 contact residues identified from a crystal structure[10] are conserved between human and *C. elegans* p53 (5 out of 8 residues are conserved). The ability of *C. elegans* p53 to interact with human ASPP family members in vitro highlights the importance of these conserved residues.

Remarkably, *C. elegans* p53 induces apoptosis very effectively in human cells. Similar to human p53, the apoptotic function of *C. elegans* p53 is positively and negatively regulated by the human ASPP and iASPP, respectively. These results demonstrate for the first time that the apoptotic function of p53 is conserved despite the limited sequence homology between human and *C. elegans* p53. The few key residues conserved between human and *C. elegans* p53 are sufficient for ASPP family members to regulate the apoptotic function of p53 both in vitro and in vivo.

The *C. elegans* p53 showed little ability to transactivate human p53 target genes such as Bax and PIG3 in comparison to human p53 (data not shown). Even though Bax is frequently a p53 target gene during apoptosis, it is not the only target gene that is required for p53 induced apoptosis. p53 is known to transactivate over 20 pro-apoptotic genes none of which has so far proved to be indispensable in p53 induced apoptosis. There are over 4000 putative p53 target genes in the human genome and many of them are pro-apoptotic genes[11]. It is possible that Ce-p53 might transactivate some of these other human p53 target genes as effectively as human p53. Unfortunately none of the ones we tested so far belong to this category. Although transactivation of the human Bax-luc reporter in human cells by Ce-p53 is not very strong, it is important to point out that the co-expression of ASPP stimulated the transactivation function of Ce-p53 only on the promoters of Bax but not on mdm2. This pattern of ASPP action is similar to that seen with human p53. Alternatively, Ce-p53 might induce apoptosis independent of its transcriptional activity; human p53 is known to induce apoptosis through both transcriptional dependent and independent pathways[12]. Regardless of how Ce-p53 induces apoptosis in human cells, the most remarkable and important fact is that the human ASPP family of proteins regulate the apoptotic function of both Ce-p53 and human p53 in a similar way. Ce-iASPP is also able to completely replace human iASPP in all the assays performed in human cells. These results argue strongly that the regulation of p53 function by ASPP family is conserved from worm to human. The link between p53 and the ASPP family suggests that the regulation of p53 by the ASPP family should be the future target in developing new strategies for cancer therapy. Tumours expressing wild type p53 can be sensitised to treatments by enhancing the activity of ASPP and removing the activity of iASPP.

Chemotherapy Drugs Appear to Modify ASPP Family Protein Function

As 50% of human tumours maintain wild-type p53, one approach to treating cancer might be to reactivate p53 in tumour cells to induce apoptosis. Indeed, chemotherapy and radiotherapy agents generate DNA damage, which could activate functional p53 in tumour cells. However, the pathways affected by these drugs differ and tumour cells can develop protective strategies to enable survival. As mentioned previously, ASPP1 and ASPP2 specifically enhance the apoptotic function of p53 by stimulating the DNA binding and transactivation function of p53 on the promoters of proapoptotic genes (Samuels-Lev et al., 2001), while iASPP is a very conserved inhibitor of p53 (Bergamaschi et al., 2003). Taken together, this suggests that the function of the ASPP family of proteins may be affected by chemotherapy agents, which in turn vary the subsequent p53 apoptotic response, and thus play a role in the effectiveness of drugs used in cancer treatment.

Specifically, experiments were carried out to investigate the hypothesis that chemotherapy drugs could be made more effective in cell lines undergoing DNA damage by modulating the activity of the ASPPs.

Chemotherapy agents were used to investigate whether the apoptosis induced in cell lines correlated directly with p53 expression levels. U-2OS and MCF7 cells were transfected with the Pig3 promoter (Pig3-luc 17mer) and treated with various chemotherapy drugs (doxorubicin, cisplatin, etoposide, colchicine, deferoxamine mesylate (DFO), daunorubicin, camptothecin and 5'fluorouracil).

Luciferase levels were assayed 24 hours later, FIG. 13. The results illustrate that drug-induced apoptosis, as measured by luciferase, did not correlate directly with p53 protein levels (for example, compare doxorubicin and cisplatin responses) indicating that p53 alone is not responsible for the activation of proapoptotic genes. It is possible that the ASPP proteins respond differently to the various chemotherapy drugs to give the discrepancy observed between Pig3 activation and p53 protein expression level.

To test whether the ASPPs play a role in the process, short interfering RNA (si-RNA) (Elbashir et al., 2001) and antisense RNA were used to knock down ASPP gene expression. Sequences to generate si-RNA were cloned into pSuper plasmid (Brummelkamp et al., 2002). Since responses of proapoptotic genes differed depending on the drug used, both doxorubicin and cisplatin were tested in U-2OS cells. Pig3-luciferase was transfected together with either antisense or si-iASPP (FIGS. 14A and 14B). The results show that antisense ASPP1 or antisense ASPP2 both reduce the induction of Pig3-luciferase by doxorubicin (FIG. 14A) but antisense or si-RNA for iASPP caused no reduction. A si-RNA for p53 prevented the doxorubicin response (FIG. 14A). In contrast, antisense ASPP1 or antisense ASPP2 had little effect on the cisplatin induction of the Pig3 promoter but the si-RNA for iASPP caused a significant increase. Again siRNA for p53 prevented the cisplatin response.

These data could be interpreted to indicate that endogenous p53 activity was induced by doxorubicin cooperating with ASPP1 and ASPP2 in U-2OS cells but in response to cisplatin endogenous p53 activity was being restrained by iASPP. These differential effects might be due to the modulatory effects of the drugs on ASPP or iASPP activity.

The Disruption of iASPP/p53 Binding Can Enhance Apoptosis and Could Potentially be Used in Cancer Therapy Inhibiting the p53/iASPP interaction with synthetic molecules should lead to p53-mediated apoptosis in p53-positive stressed cells.

Figure 10:
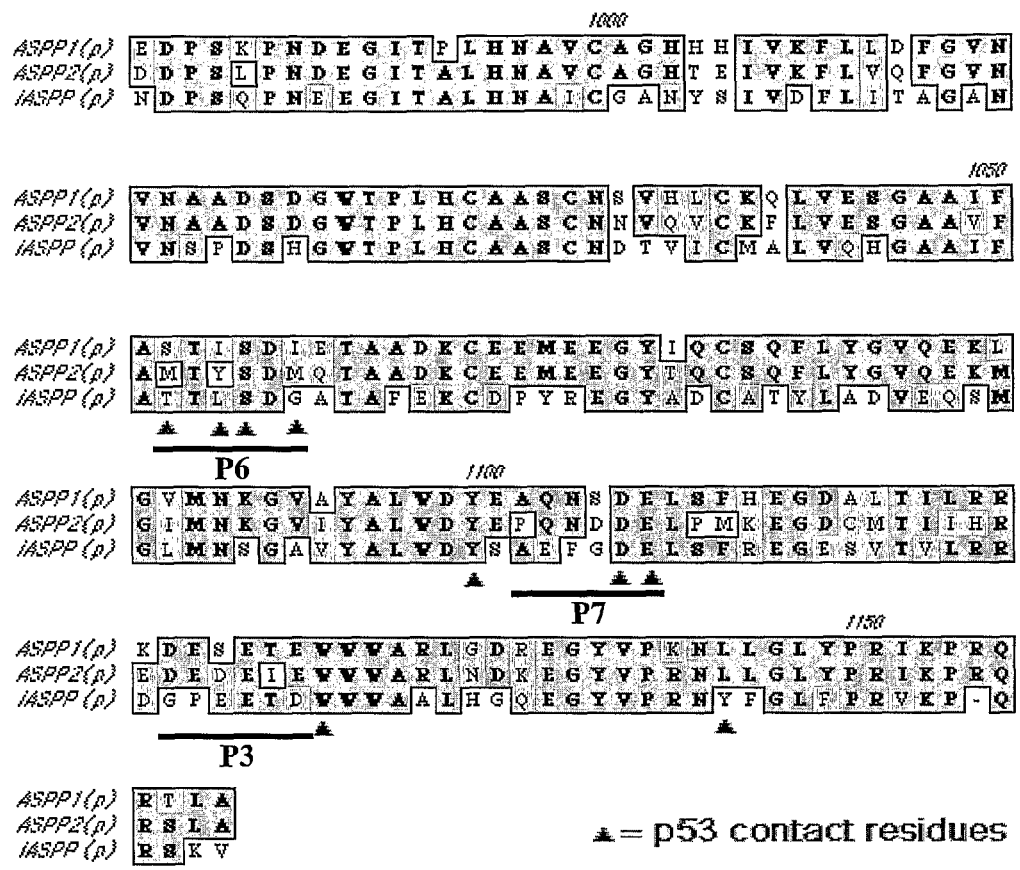
FIG. 10 illustrates p53 contact sites in iASPP.

It is known that p53 binds to the C terminal part of iASPP; specific contact amino acids are indicated in FIG. 10. Three different peptides containing particular iASPP sequences were designed to inhibit the iASPP/p53 binding and test the effects on proapoptotic genes, FIG. 10. The three peptides were linked to a Tat sequence and to FITC.

The peptides were initially tested for their effects on p53 transactivation of the Bax promoter using UV radiation to activate p53, FIG. 11. The luciferase activity of the Bax promoter was only slightly affected by the control peptide, which should not affect iASPP & p53 interaction. However, addition of peptide 3, 6 or 7 caused about a two fold increase in the reporter activity, using 50 μM peptide. Some peptides were less active at 100 μM.

The study was continued with the Pig3-luciferase reporter. The Pig3 gene is transactivated by p53 in a different way to Bax. Whereas Bax is transactivated by a conventional transcription domain (El-Deiry et al., 1992) (Bourdon et al., 1997), p53 binds to the Pig3 promoter via repeat sequences (TGYCC)n, where Y=C or T (Polyak et al., 1997). The number of repeats is polymorphic within populations (Contente et al., 2002). Two reporters containing 10 or 17 repeats were used in case there was a difference in response between them. Other variables to consider are time and concentration of peptide and the location of the peptides in the cells since p53 and iASPP are mostly nuclear proteins.

A second generation of peptides was used for this experiment, which are identical to the previous ones except for the tag. These peptides were tagged with nine arginine residues, which are thought to give the peptides better penetration into cells (Lindsay, 2002). In this case a peptide 7 from the ASPP2 sequence was included (see FIG. 10) and a different control peptide (Yap) was used. Cells were treated with cisplatin and peptides were applied for 12 hours at two different concentrations (25 uM and 50 uM) and the results are shown in FIG. 15. Despite some variability in the results the P3-iASPP or P7-iASPP peptides showed a substantial increase in the reporter activity over the response seen with control Yap peptide and cisplatin treatment, suggesting that apoptosis induced during chemotherapy could be enhanced through the use of iASPP peptide inhibitors.

TABLE 1

|  | Human | Mouse | C. El. | Drosophila | Fugu I | Fugu II | Fugu III | Fugu IV |
|---|---|---|---|---|---|---|---|---|
| Human (352) | X | X | X | X | X | X | X | X |
| Mouse (260) | 93.7 | X | X | X | X | X | X | X |
| C. El. (769) | 20.4 | 38.8 | X | X | X | X | X | X |
| Drosophila (1071) | 43.2 | 40.0 | 32.4 | X | X | X | X | X |
| Fugu I (260) | 51.9 | 45.0 | 48.1 | 55.4 | X | X | X | X |
| Fugu II (252) | 54.8 | 54.8 | 51.6 | 58.7 | X | X | X | X |
| Fugu III (144) | 54.2 | 53.5 | 54.2 | 64.6 | X | X | X | X |
| Fugu IV (132) | 51.5 | 50.8 | 55.3 | 62.9 | X | X | X | X |

The invention claimed is:

1. An isolated peptide consisting of an amino acid sequence selected from the group consisting of: DGPEETD (SEQ ID NO: 2); GPEETD (SEQ ID NO: 1); TTLSDG (SEQ ID NO: 3); AEFGDE (SEQ ID NO: 8, amino acids 294-299); or PRNYFG (SEQ ID NO: 4).

2. An isolated peptide that is 6-20 amino acids in length and that comprises the sequence AEFGDE (SEQ ID NO: 8, positions 294-299), wherein the isolated peptide is capable of inhibiting iASPP binding to p53.

3. An isolated peptide consisting of:
   (a) an amino acid sequence selected from the group consisting of: DGPEETD (SEQ ID NO: 2); GPEETD (SEQ ID NO: 1); TTLSDG (SEQ ID NO: 3); AEFGDE (SEQ ID NO: 8, amino acids 294-299); or PRNYFG (SEQ ID NO: 4); and (b) an arginine tag.

4. A composition comprising the peptide according to claim 1 and a carrier, diluent, or excipient.

5. A composition comprising at least one peptide according to claim 1 or claim 2 and at least one anti-cancer agent.

6. The composition according to claim 5 wherein said anticancer agent is selected from the group consisting of: cisplatin; carboplatin; cyclophosphamide; melphalan; carmusline; methotrexate; 5-fluorouracil; cytarabine; mercaptopurine; daunorubicin; doxorubicin; epirubicin; vinblastine; vincristine; dactinomycin; mitomycin C; taxol; L-asparaginase; G-CSF; etoposide; colchicine; derferoxamine mesylate; and camptothecin.

7. The composition according to claim 6 wherein said anticancer agent is cisplatin.

8. The composition according to claim 6 wherein said anticancer agent is doxorubicin.

9. A complex comprising the peptide according to claim 1 or claim 2 and an antibody, or antigen-binding domain thereof.

10. The complex according to claim 9 wherein said antibody or antigen binding domain is a cell-specific antibody.

11. The complex according to claim 9 wherein said antibody is a cancer cell-specific antibody.

12. An isolated peptide consisting of amino acids AEFGDE (SEQ ID NO: 8, amino acids 294-299) attached to an arginine tag.

13. A composition comprising the peptide according to claim 12 and at least one anti-cancer agent.

14. A complex comprising the peptide according to claim 12 and an antibody or antigen-binding domain thereof.

15. The peptide of claim 2, wherein the peptide includes an arginine tag.

16. The peptide of claim 15, wherein the arginine tag contains 2-10 residues.

* * * * *